(12) United States Patent
Kadoguchi et al.

(10) Patent No.: US 9,331,001 B2
(45) Date of Patent: May 3, 2016

(54) SEMICONDUCTOR MODULE

(75) Inventors: Takuya Kadoguchi, Toyota (JP); Yoshikazu Suzuki, Toyota (JP); Masaya Kaji, Toyota (JP); Kiyofumi Nakajima, Chigasaki (JP); Tatsuya Miyoshi, Nagoya (JP); Takanori Kawashima, Anjo (JP); Tomomi Okumura, Toyota (JP)

(73) Assignee: TOYOTA JIDOSHA KABUSHIKI KAISHA, Toyota-Shi (JP)

( * ) Notice: Subject to any disclaimer, the term of this patent is extended or adjusted under 35 U.S.C. 154(b) by 0 days.

(21) Appl. No.: 13/819,209

(22) PCT Filed: Sep. 2, 2010

(86) PCT No.: PCT/JP2010/065062
§ 371 (c)(1),
(2), (4) Date: Feb. 26, 2013

(87) PCT Pub. No.: WO2012/029165
PCT Pub. Date: Mar. 8, 2012

(65) Prior Publication Data
US 2013/0154084 A1 Jun. 20, 2013

(51) Int. Cl.
*H01L 23/40* (2006.01)
*H01L 23/31* (2006.01)
(Continued)

(52) U.S. Cl.
CPC .............. *H01L 23/40* (2013.01); *H01L 23/3121* (2013.01); *H01L 23/3735* (2013.01); *H01L 23/4006* (2013.01); *H01L 23/4334* (2013.01); *H01L 23/473* (2013.01); *H01L 23/49548* (2013.01); *H01L 24/36* (2013.01); *H01L 24/40* (2013.01); *H01L 24/73* (2013.01); *H01L 24/45* (2013.01); *H01L 24/48* (2013.01); *H01L 25/072* (2013.01); *H01L 2224/32245* (2013.01);
(Continued)

(58) Field of Classification Search
CPC ......... H01L 23/36; H01L 25/07; H01L 25/18; H01L 23/40
USPC .......... 257/717, 714, 723, 712, 731, 732, 733
See application file for complete search history.

(56) References Cited

U.S. PATENT DOCUMENTS 4,707,722 A * 11/1987 Folk et al. ..................... 257/741
2001/0014029 A1* 8/2001 Suzuki et al. ................. 363/141
(Continued)

FOREIGN PATENT DOCUMENTS

JP 2001-308246 A 11/2001
JP 2007184315 A 7/2007
(Continued)

Primary Examiner — Matthew Reames
Assistant Examiner — Vincent Wall
(74) Attorney, Agent, or Firm — Kenyon & Kenyon LLP

(57) ABSTRACT

A semiconductor module includes a semiconductor device; a metal plate portion that includes a first surface on a side of the semiconductor device and has a fastening portion at an end thereof; a molded portion that is formed by molding a resin on the semiconductor device and the metal plate portion, a cooling plate portion that is a separate member from the metal plate portion, is provided on a side opposite to the first surface on the side of the semiconductor device, and includes fins on a side opposite to the side of the metal plate portion; wherein the fastening portion of the metal plate portion is exposed out of the molded portion, and the cooling plate portion includes a fastening portion at a position that corresponds to a position of the fastening portion of the metal plate portion.

1 Claim, 16 Drawing Sheets

(51) Int. Cl.
*H01L 23/373* (2006.01)
*H01L 23/433* (2006.01)
*H01L 23/473* (2006.01)
*H01L 23/495* (2006.01)
*H01L 25/07* (2006.01)
*H01L 23/00* (2006.01)

(52) U.S. Cl.
CPC ............... *H01L2224/40095* (2013.01); *H01L 2224/40225* (2013.01); *H01L 2224/45124* (2013.01); *H01L 2224/48091* (2013.01); *H01L 2224/48247* (2013.01); *H01L 2224/73221* (2013.01); *H01L 2924/014* (2013.01); *H01L 2924/01029* (2013.01); *H01L 2924/1305* (2013.01); *H01L 2924/1306* (2013.01); *H01L 2924/13055* (2013.01); *H01L 2924/13091* (2013.01); *H01L 2924/181* (2013.01)

(56) References Cited

U.S. PATENT DOCUMENTS

| | | | |
|---|---|---|---|
| 2007/0216013 | A1 | 9/2007 | Funakoshi et al. |
| 2008/0224303 | A1 | 9/2008 | Funakoshi et al. |
| 2010/0133684 | A1* | 6/2010 | Oka et al. ............... 257/712 |

FOREIGN PATENT DOCUMENTS

| | | | | |
|---|---|---|---|---|
| JP | 2007251076 | A | | 9/2007 |
| JP | 2008-103502 | A | | 5/2008 |
| JP | 2008103502 | A | * | 5/2008 |
| JP | 2008124430 | A | | 5/2008 |
| JP | 2008-186958 | A | | 8/2008 |
| JP | 2009-070934 | A | | 4/2009 |
| JP | 2009-296708 | | | 12/2009 |
| JP | 2009296708 | A | * | 12/2009 |
| JP | 2010-114257 | A | | 5/2010 |
| JP | 2010-129868 | A | | 6/2010 |

* cited by examiner

FORMING AREA OF
COOLING FINS 573a

FIG.16

| i (ELEMENT EXAMPLE) | $t_i$ (m : ELEMENT THICKNESS) | $c_i$ (m/s : VELOCITY OF SOUND) |
|---|---|---|
| 5 (SEMICONDUCTOR DEVICE) | $t_5$ | $c_5$ |
| 4 (SOLDER LAYER) | $t_4$ | $c_4$ |
| 3 (METAL BLOCK) | $t_3$ | $c_3$ |
| 2 (INSULATING SHEET) | $t_2$ | $c_2$ |
| 1 (METAL PLATE PORTION) | $t_1$ | $c_1$ |
| 0 (WATER) | $t_0$ | $c_0$ |

FIG.17

| i (ELEMENT EXAMPLE) | $t_i$ (m : ELEMENT THICKNESS) | $c_i$ (m/s : VELOCITY OF SOUND) |
|---|---|---|
| 5 (SEMICONDUCTOR DEVICE) | – | – |
| 4 (SOLDER LAYER) | 0.15mm | 2500 |
| 3 (METAL BLOCK) | 3.00mm | 4700 |
| 2 (INSULATING SHEET) | 0.20mm | 4000 |
| 1 (METAL PLATE PORTION) | $t_1$ | 6420 |
| 0 (WATER) | – | – |

SEMICONDUCTOR MODULE

CROSS-REFERENCE TO RELATED APPLICATIONS

This application is a 371 national phase application of PCT/JP2010/065062 filed 2 Sep. 2010, the contents of which is incorporated herein by reference in its entirety.

TECHNICAL FIELD

The present invention is related to a semiconductor module, etc., which includes a molded portion of a resin.

BACKGROUND ART

Conventionally, a power semiconductor module is known which includes: a circuit board comprising a metal base plate, a high thermal conduction insulation layer, and a wiring pattern; a semiconductor device for power joined to an element mount section of the wiring pattern; a cylindrical external terminal connection body that is installed in the wiring pattern electrically connected to the semiconductor device for power and to which an external terminal is inserted and connected; a through hole that is formed on the metal base plate and fixes a cooling fin mounted to a surface at the other side of the metal base plate to the metal base plate by a mount member; and a transfer mold resin body sealed to cover one side and a side face of the metal base plate, and the semiconductor device for power while a surface at the other side of the metal base plate and an upper portion of the cylindrical external terminal connection body are exposed, and an insertion hole section of the mount member communicating with the through hole and having a diameter larger than that of the through hole is formed.

[Patent Document 1] Japanese Patent

DISCLOSURE OF INVENTION

Problem to be Solved by Invention

With respect to the semiconductor module which includes a molded portion of a resin, it may be necessary to inspect a status of an inside of the molded portion with ultrasonic test equipment, etc.

Therefore, an object of the present invention is to provide a semiconductor module, etc., which has a configuration in which a status of an inside of a molded portion can be easily inspected with ultrasonic test equipment, etc.

Means to Solve the Problem

According to an aspect of the present invention a semiconductor module is provided, which includes
 a semiconductor device;
 a metal plate portion that includes a first surface on a side of the semiconductor device and has a fastening portion at an end thereof;
 a molded portion that is formed by molding a resin on the semiconductor device and the metal plate portion,
 a cooling plate portion that is a separate member from the metal plate portion, is provided on a side opposite to the first surface on the side of the semiconductor device, and includes fins on a side opposite to the side of the metal plate portion;
 wherein the fastening portion of the metal plate portion is exposed out of the molded portion, and the cooling plate portion includes a fastening portion at a position that corresponds to a position of the fastening portion of the metal plate portion.

Advantage of the Invention

According to the present invention, a semiconductor module, etc., can be obtained which has a configuration in which a status of an inside of a molded portion can be easily inspected with ultrasonic test equipment, etc.

BRIEF DESCRIPTION OF DRAWINGS

FIG. 16 is a table for illustrating a definition of variables used in the way of deriving the appropriate range of a thickness t1 of the metal plate portion 50.

FIG. 17 is a table for illustrating a condition used to calculate the appropriate range of a thickness t1 of the metal plate portion 50.

BEST MODE FOR CARRYING OUT THE INVENTION

In the following, the best mode for carrying out the present invention will be described in detail by referring to the accompanying drawings.

Figure 1:
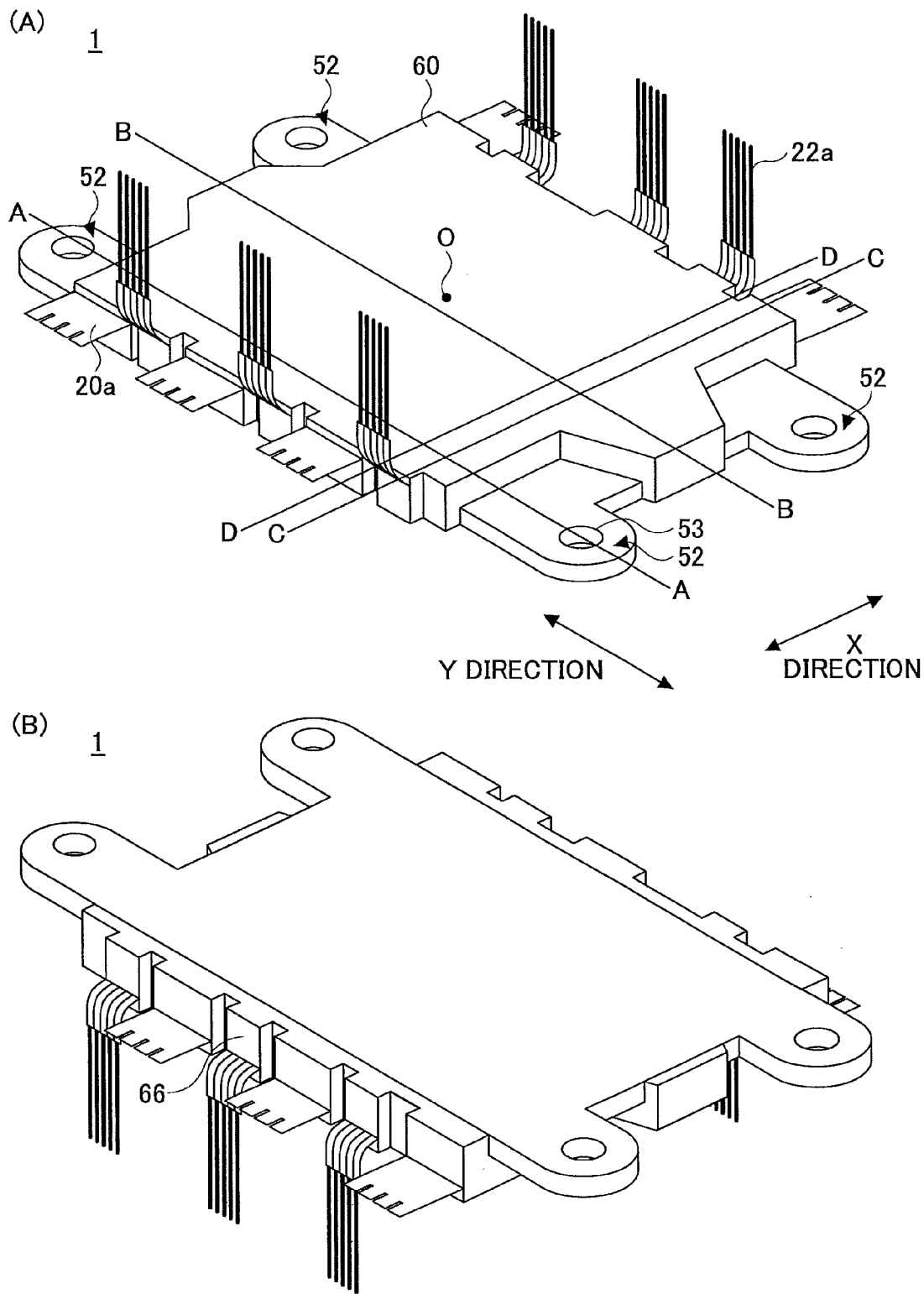
FIG. 1 is a perspective view from above for illustrating an appearance of a semiconductor module 1 according to one embodiment (a first embodiment) of the present invention.
Figure 2:
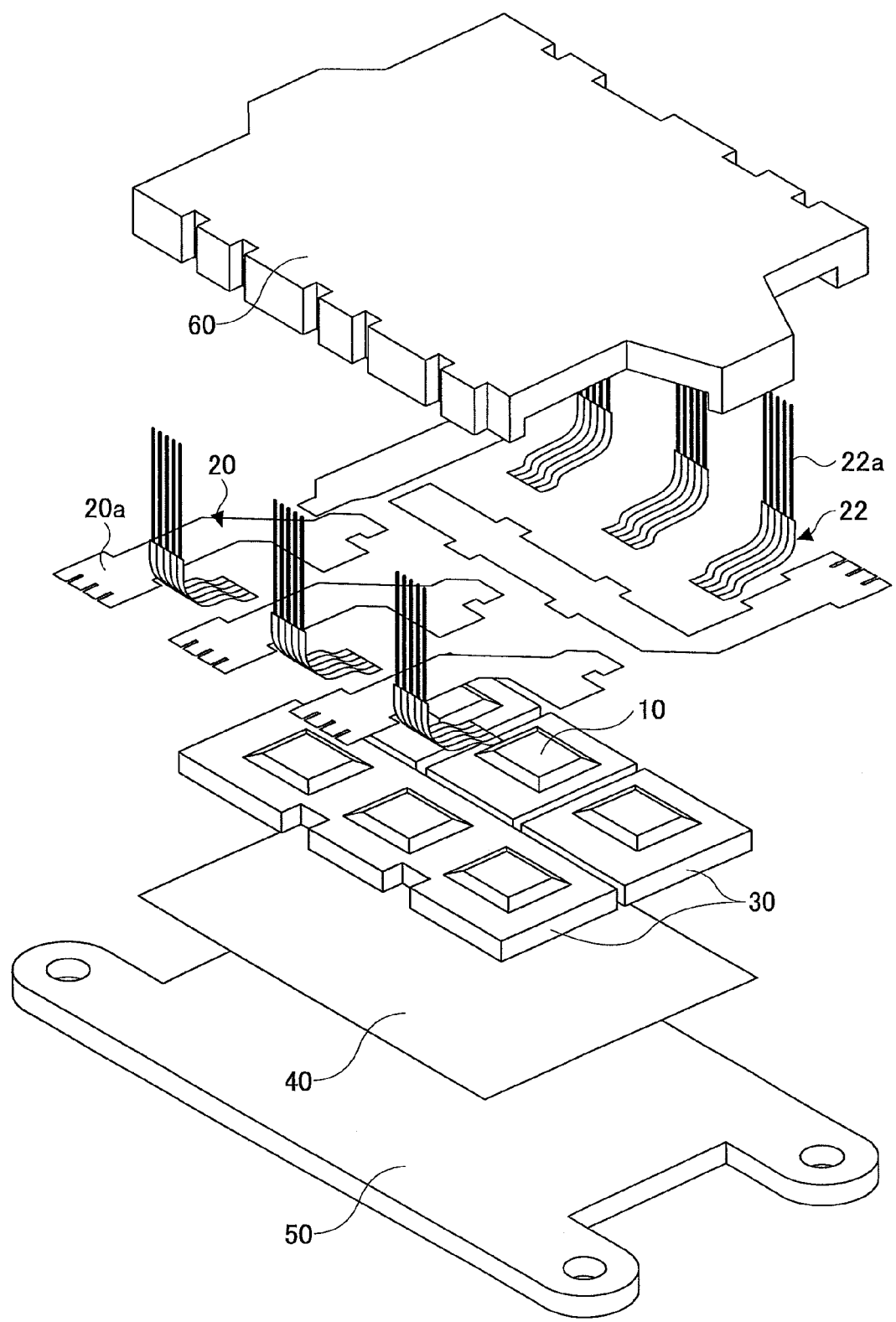
FIG. 2 is a perspective view of an example of main parts of the semiconductor module 1 in FIG. 1 which are exploded for the sake of convenience.

FIG. 1 is a perspective view illustrating an example of an appearance of the semiconductor module 1 according to an embodiment (a first embodiment) of the present invention, where (A) is a perspective view from an upper side and (B) is a perspective view from a lower side. It is noted that the up and down directions are different depending on the installed status; however, hereinafter a metal plate portion side of the semiconductor module 1 is assumed to be a lower side for the sake of convenience. Further, as terminology, "center side" is used with reference to a center O of the semiconductor module 1 (see FIG. 1 (A)). It is noted that the center O may be rough and does not have a nature which is determined precisely. FIG. 2 is a perspective view of an example of main parts of the semiconductor module 1 in FIG. 1 which are exploded for the sake of convenience.

In the illustrated example, the semiconductor module 1 is a part of an inverter for driving a motor used in a hybrid vehicle or an electric vehicle.

Figure 3:
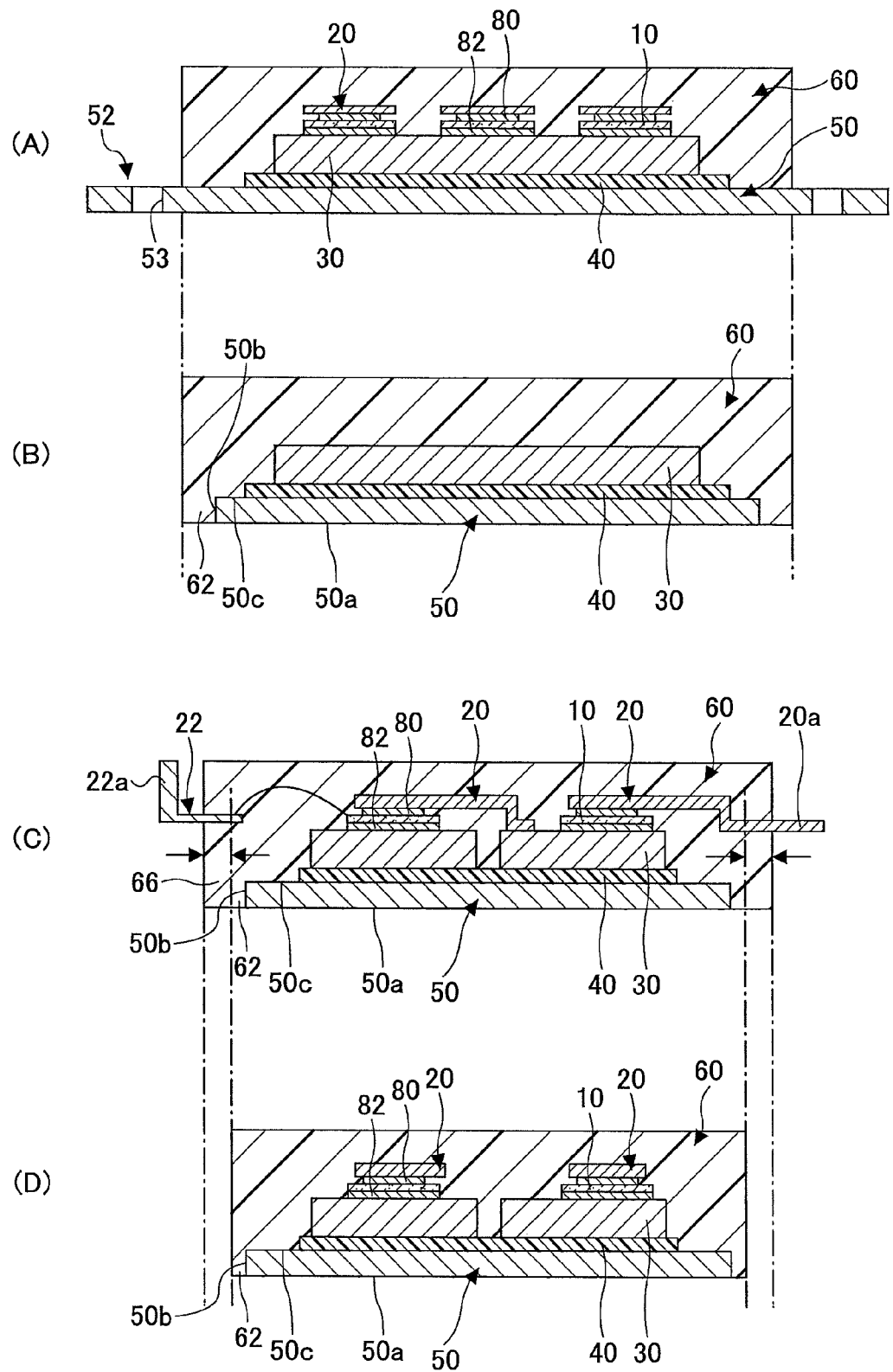
FIG. 3 is a cross-sectional view of the semiconductor module 1 in FIG. 1 along the respective lines.

FIG. 3 is a cross-sectional view of the semiconductor module 1 in FIG. 1 along the respective lines, where (A) is a cross-sectional view along line A-A, (B) is a cross-sectional view along line B-B, (C) is a cross-sectional view along line C-C and (D) is a cross-sectional view along line D-D. It is noted in FIGS. 1 through 3 a status in which a cooling plate portion 57 is not attached is illustrated for the sake of convenience.

Figure 4:
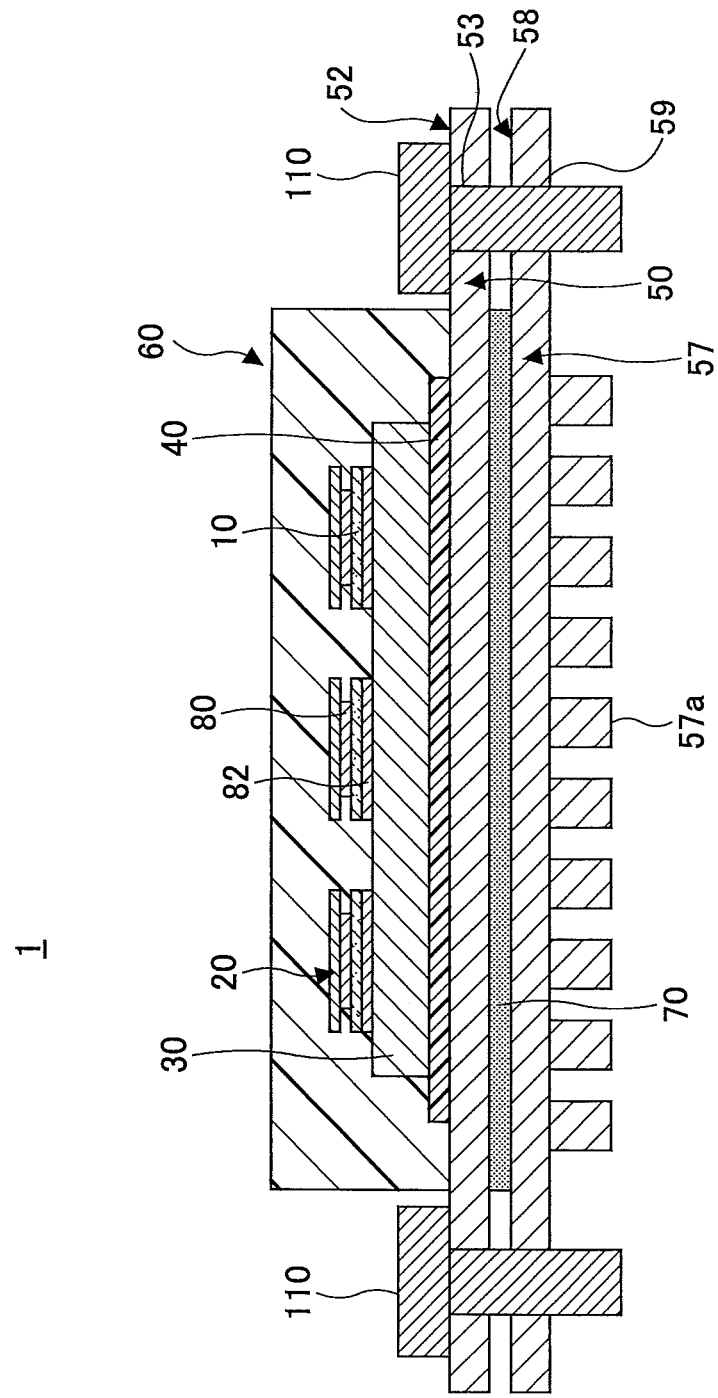
FIG. 4 is a cross-sectional view of the semiconductor module 1 in a status in which a cooling plate portion 57 is attached.

FIG. 4 is a cross-sectional view of the semiconductor module 1 in a status in which a cooling plate portion 57 is attached, when the semiconductor module 1 is cut along a line A-A in FIG. 3.

The semiconductor module 1 includes as main components, semiconductor devices 10, wiring members 20, 22, metal blocks 30, an insulating sheet 40, a metal plate portion 50, a cooling plate portion 57 (see FIG. 4) and a resin molded portion 60.

The semiconductor devices 10 include a power semiconductor device. For example, the semiconductor devices 10 may include a switching device such as an IGBT (Insulated Gate Bipolar Transistor) and a MOSFET (metal oxide semiconductor field-effect transistor). It is noted that in the illustrated example, the semiconductor module 1 is a part of the inverter, and the semiconductor devices 10 may be IGBTs and diodes which define respective upper arms and lower arms of a U-phase, a V-phase and a W-phase arranged in parallel between a positive side line and a negative side line.

The wiring members 20, 22 are constructed by forming a metal plate (a lead frame substrate). In the illustrated example, the wiring members 20 are wiring members used for a power supply line (i.e., leads for a power supply line). Further, the wiring members 22 are pin-shaped wiring members used for a signal transmission (i.e., leads for a signal transmission). The wiring members 20 may be connected to the corresponding terminals semiconductor devices 10 by soldering, etc. In the illustrated example, the wiring members 20 are connected to the corresponding terminals of the semiconductor devices 10 via solder layers 80. Further, the wiring members 22 may be connected to the corresponding semiconductor devices 10 by wire bonding (aluminum wires), etc. For example, with respect to IGBTs, some of the wiring members 20 are connected to collectors of the IGBTs via the metal blocks 30. Further, some of the wiring members 20 are connected to emitters of the IGBTs. Further, some of the wiring members 22 are connected to gates of the IGBTs.

The metal blocks 30 have a heat sink function of absorbing heat, such as transient heat, and spreading it. The metal blocks 30 may be formed of any material other than a metal material as long as they have a heat sink function; however, preferably the metal blocks 30 are formed of a metal material which has good thermal diffusivity, such as copper. On upper surfaces of the metal blocks 30 are disposed the semiconductor devices 10 by soldering, etc. In the illustrated example, the semiconductor devices 10 are installed on the upper surfaces of the metal blocks 30 via solder layers 82. The metal blocks 30 mainly absorb the heat generated in the semiconductor devices 10 during the operations of the semiconductor devices 10 and diffuse the heat toward the insides thereof.

The insulating sheet 40 is formed of a resin sheet, for example. The insulating sheet 40 enables high thermal conductivity from the metal blocks 30 to the metal plate portion 50 while ensuring electrical insulation between the metal blocks 30 and the metal plate portion 50. The insulating sheet 40 has an outer shape which is larger than a lower surface of the metal blocks, as illustrated in FIG. 3, etc.

It is noted that, preferably, the insulating sheet 40 bonds to the metal blocks 30 and the metal plate portion 50 directly without using solder, metal films or the like. With this arrangement, it is possible to reduce thermal resistance and simplify a process in comparison with the case of using the solder. Further, the surface treatment on the metal plate portion 50 suited for soldering becomes unnecessary. For example, the insulating sheet 40 is made of the same resin material (epoxy resin, for example) as the resin molded portion 60 described hereinafter, and bonds to the metal blocks 30 and the metal plate portion 50 under a pressure and at a temperature at the time of molding the resin molded portion 60 described hereinafter.

The metal plate portion 50 and the cooling plate portion 57 have substantially the same outline, and are stacked in the vertical direction, as illustrated in FIG. 4. It is noted that the cooling plate portion 57 may not be attached to the metal plate portion 50 before the installation stage of the semiconductor module1, or may be pre-assembled using bolts 110, etc., as illustrated in FIG. 4.

The metal plate portion 50 includes fastening portions 52 on the opposite sides thereof in a direction (Y direction in FIG. 1, in this example). The respective fastening portions 52 provide bolt seating surfaces in which mounting holes 53 through which bolts are tighten are formed. The metal plate portion 50 may be fastened to a channel forming member (a water channel, a housing, etc.) which defines a cooling medium channel through which the cooling medium is circulated (see FIG. 6).

The fastening portions 52 of the metal plate portion 50 are formed in areas at the ends of the metal plate portion 50, which areas project in the Y direction with respect to their neighboring areas, as illustrated in FIG. 1, etc. Specifically, in the example illustrated in FIG. 1, the fastening portions 52 are formed at two locations on each end, and the two fastening portions 52 on each end are formed in areas, which areas are located on the opposite sides in an X direction and project in a Y direction with respect to a middle area therebetween. It is noted that the fastening portions 52 of the metal plate portion 50 are integrally formed with the metal plate portion 50 by pressing, for example; however, the fastening portions 52 may be formed separately and fixed to the metal plate portion 50 by welding or the like.

The cooling plate portion 57 is a plate member whose outline is substantially the same as that of the metal plate portion 50. The cooling plate portion 57 is formed of a material which has good thermal diffusivity. For example, the cooling plate portion 57 may be formed of a metal such as aluminum. The cooling plate portion 57 has fins 57a on a lower surface thereof. The number of the fins 57a and an arrangement manner of the fins 57a are arbitrary unless otherwise specified (see configurations illustrated in FIG. 11, etc.). Further, a configuration of fins 57a, such as a shape, height, etc., is arbitrary. The fins 57a may be straight fins or pin-shaped fins arranged in a staggered arrangement or the like. In an installed status of the semiconductor module 1 the fins 57a come into contact with a cooling medium such as cooling water or cooling air. In this way, the heat generated in the semiconductor devices 10 during the operations of the semiconductor devices 10 is transferred to the cooling medium from the fins 57a of the metal plate portion 50 via the metal blocks 30, the insulating sheet 40 the metal plate portion 50 and the cooling plate portion 57.

It is noted that the fins 57a may be integrally formed with the cooling plate portion 57 (aluminum die-casting, for example) or may be integrated with the cooling plate portion 57 by welding or the like.

The cooling plate portion 57 includes fastening portions 58 at positions corresponding to positions of the fastening portions 52 of the metal plate portion 50. The fastening portions 58 includes mounting holes 59 through which bolts are tighten at positions corresponding to the positions of the mounting holes 53 of the metal plate portion 50. The cooling plate portion 57 is fastened to a channel forming member (see FIG. 6) together with the metal plate portion 50.

Preferably, grease 70 is applied between the metal plate portion 50 and the cooling plate portion 57. The grease 70 may have high thermal conductivity. With this arrangement, even if a clearance between the metal plate portion 50 and the cooling plate portion 57 is increased due to bowing or the like, heat can be dissipated via the grease 70.

Here, according to the present embodiment, as described above, since the metal plate portion 50 and the cooling plate portion 57 are separate members, the cooling plate portion 57 can be easily removed from the semiconductor module 1. Thus, the semiconductor module 1 can be subject to various inspections with a status in which the cooling plate portion 57 is removed, which facilitates the inspections. For example, a status of the inside (an inspection of whether there are exfoliations between the respective layers or an inspection of whether there are voids in the layers etc.) of the molded portion 60 can be easily inspected with ultrasonic test equipment (SAT: Scanning Acoustic Tomography). Specifically, when the inside of the semiconductor module 1 (the inside of the resin molded portion 60, etc.) is inspected with ultrasonic test equipment, ultrasonic waves need to be radiated from the side of the lower surface of the semiconductor module 1; however, if there are fins 57a on the lower surface of the semiconductor module 1, ultrasonic waves may reflect at the fins 57a, and thus precise inspection results cannot be obtained. In contrast, according to the semiconductor module 1 of the present embodiment, it is possible to perform the ultrasonic inspection of the semiconductor module 1 with high accuracy by removing the cooling plate portion 50 with the fins 57a or before the cooling plate portion 50 is installed. It is noted that the concrete inspection target may include the presence or absence of exfoliation between the semiconductor devices 10 and the solder layers 82, the presence or absence of voids inside the solder layers 82, the presence or absence of exfoliation between the solder layers 82 and the metal blocks 30, the presence or absence of exfoliation between the metal blocks 30 and the insulating sheet 40, the presence or absence of exfoliation between the insulating sheet 40 and the cooling plate portion 50, etc.

The resin molded portion 60 is formed by molding a resin on the semiconductor devices 10, the wiring members 20, 22, the metal blocks 30, the insulating sheet 40 and the metal plate portion 50, as illustrated in FIG. 3, etc. Specifically, the resin molded portion 60 is a portion for sealing therein the main components (the semiconductor devices 10, the wiring members 20, 22, the metal blocks 30 and the insulating sheet 40) with respect to the upper surface of the metal plate portion 50. It is noted that the resin used may be epoxy resin, for example. However, with respect to the wiring members 20 and 22, the terminal portions 20a, 22a for connecting to peripheral devices are exposed out of the resin molded portion 60. Further, the fastening portions 52 of the metal plate portion 50 are exposed out of the resin molded portion 60. Specifically, in the metal plate portion 50 the fastening portions 52 are set outwardly (in the Y direction) with respect to an area adhered to the resin molded portion 60. It is noted that the terminal portions 20a, 22a of the wiring members 20, may be changed to their final shapes by lead cutting and forming after the resin molded portion 60 is molded.

Here, according to the embodiment, as illustrated in FIG. 1, FIG. 3 (A), (C), etc., the terminal portions 20a, 22a of the wiring members 20, 22 are exposed out of the resin molded portion 60 to extend in the X direction while the fastening portions 52 of the metal plate portion 50 are exposed out of the resin molded portion 60 to extend in the Y direction. Specifically, the terminal portions 20a, 22a of the wiring members 20, 22 and the fastening portions 52 of the metal plate portion 50 are exposed out of the resin molded portion 60 in the perpendicular directions. In other word, the terminal portions 20a, 22a of the wiring members 20, 22 are exposed out of the resin molded portion 60 at the opposite sides of the semiconductor module 1 in the X direction while the fastening portions 52 of the metal plate portion 50 are exposed out of the resin molded portion 60 at the opposite sides of the semiconductor module 1 in the Y direction.

According to the configuration, since the terminal portions 20a, 22a of the wiring members 20, 22 don't extend above the fastening portions 52 (the mounting holes 53, in particular) of the metal plate portion 50 viewed in a vertical direction, it is possible to bolt the fastening portions 52 of the metal plate portion 50 to the channel forming member 100 described hereinafter (see FIG. 6) directly above the fastening portions 52. Therefore, workability of bolting is improved and useless space can be eliminated.

The resin molded portion 60 preferably includes, in its side portion region from which the terminal portions 20a, 22a of the wiring members 20, are exposed, rib portions 66 which project outwardly with respect to their neighboring side portion region, as illustrated in contrast in (C) and (D) in FIG. 3. The rib portions 66 extend in a vertical direction with respect to the wiring members 20, 22 near the portions from which the wiring members 20, 22 are exposed. In other words, the rib portions 66 are provided such that they cover root portions of the terminal portions 20a, 22a of the wiring members 20, 22 (i.e., root portions with respect to the resin molded portion 60). The rib portions 66 are provided only for the side portion region from which the terminal portions 20a, 22a of the wiring members 20, 22 are exposed. Thus, as illustrated in (B) in FIG. 1, concave portions are formed between the rib portions 66 in the side portion of the resin molded portion 60, and thus the side portion of the resin molded portion 60 have projections and depressions as a whole. With this arrangement, a creepage distance between the neighboring terminal portions 20a, 22a of the wiring members 20, 22 in the Y direction can be increased in the side portion of the resin molded portion 60.

Further, preferably, the rib portions 66 are provided not only for the exposed portions of the wiring members 20, 22 in a vertical direction but are provided over a long distance in a height direction of the side portion of the resin molded portion 60, as illustrated in (C) in FIG. 3. With this arrangement, the strength and rigidity in the end of the resin molded portion 60 can be increased. For example, with respect to the lower side, the rib portions 66 may extend to the upper surface 50c of the metal plate portion 50, or may extend to a plane which is coplanar with the lower surface 50a of the metal plate portion 50, as illustrated in (C) in FIG. 3. Further, with respect to the upper side, the rib portions 66 may extend beyond the terminal portions 20a, 22a of the wiring members 20, 22. For example, the rib portions 66 may extend to such a height that they form an upper surface of the resin molded portion 60, as illustrated in (C) in FIG. 3.

The resin molded portion 60 substantially adheres to the substantially overall wiring members 20, 22 (except for the exposed portions of the terminal portions 20a, 22a and surface portions coupled to the semiconductor devices 10); upper surfaces (except for mounting portions for the wiring members 20, 22) and side surfaces of the semiconductor devices 10; an upper surface (except for mounting portions for the semiconductor devices 10, etc.) and a side surface of the metal block 30; an upper surface (except for mounting portions for the metal block 30) and a side surface of the insulating sheet 40; and an upper surface of the metal plate portion 50, as illustrated in (C) in FIG. 3.

Further, the resin molded portion 60 preferably includes extended side portions 62 which extend such that they are coplanar with the lower surface 50a of the metal plate portion 50 to adhere to the side surface 50b of the metal plate portion 50, as illustrated in (C) in FIG. 3. With this arrangement, adhesion of the resin molded portion 60 to the side surface 50b of the metal plate portion 50 in addition to the upper surface 50c of the metal plate portion 50 is implemented, which efficiently increases adhesion between the resin molded portion 60 and the metal plate portion 50. Further, it is possible to prevent the resin molded portion 60 from being peeled off from the metal plate portion 50 due to curling of the resin molded portion 60, etc. Further, it is possible to omit a surface treatment (roughening, primer coating) in the portions of the metal plate portion 50 to which the resin molded portion 60 is adhered. However, such a surface treatment may be performed if necessary.

It is noted that with respect to the up-down direction, the extended side portions 62 may extend, from above the side surface 50b of the metal plate portion 50, to the plane which is coplanar with the lower surface 50a of the metal plate portion 50. In the example illustrated in (B) in FIG. 3, the extended side portions 62 are provided over the overall side portion of the resin molded portion 60 in a vertical direction, as is the case with the rib portions 66. It is noted that, in the illustrated example, with respect to regions where the rib portions 66 are provided, the extended side portions 62 are integral with the rib portions 66 and are defined inside of the rib portions 66 (i.e., on a side opposed to the center of the resin molded portion 60), as illustrated in (D) in FIG. 3.

Preferably, the extended side portions 62 are provided over a large area of the side surface 50b of the metal plate portion 50 so as to increase adhesion. For example, in the illustrated example, in the ends of the metal plate portion 50 in the Y direction, the extended side portions 62 are provided over the overall side surface 50b of the metal plate portion 50 except for the locations of the fastening portions 52. In other words, in the opposite ends of the metal plate portion 50 in the Y direction, the extended side portions 62 are provided on the side surface 50b of the metal plate portion 50 between two fastening portions 52 in the X direction. Further, in the opposite ends of the metal plate portion 50 in the X direction, the extended side portions 62 are provided on the side surface 50b of the metal plate portion 50 along the length of the metal plate portion 50 in the Y direction. Further, in the opposite ends of the metal plate portion 50 in the X direction, the extended side portions 62 are provided over the overall side surface 50b of the metal plate portion 50. With respect to this arrangement, since the extended side portions 62 are provided over the substantially overall side surface 50b of the metal plate portion 50 except for the locations of the fastening portions 52 of the metal plate portion 50, it is possible to effectively increase adhesion between the metal plate portion 50 and the resin molded portion 60.

Figure 5:
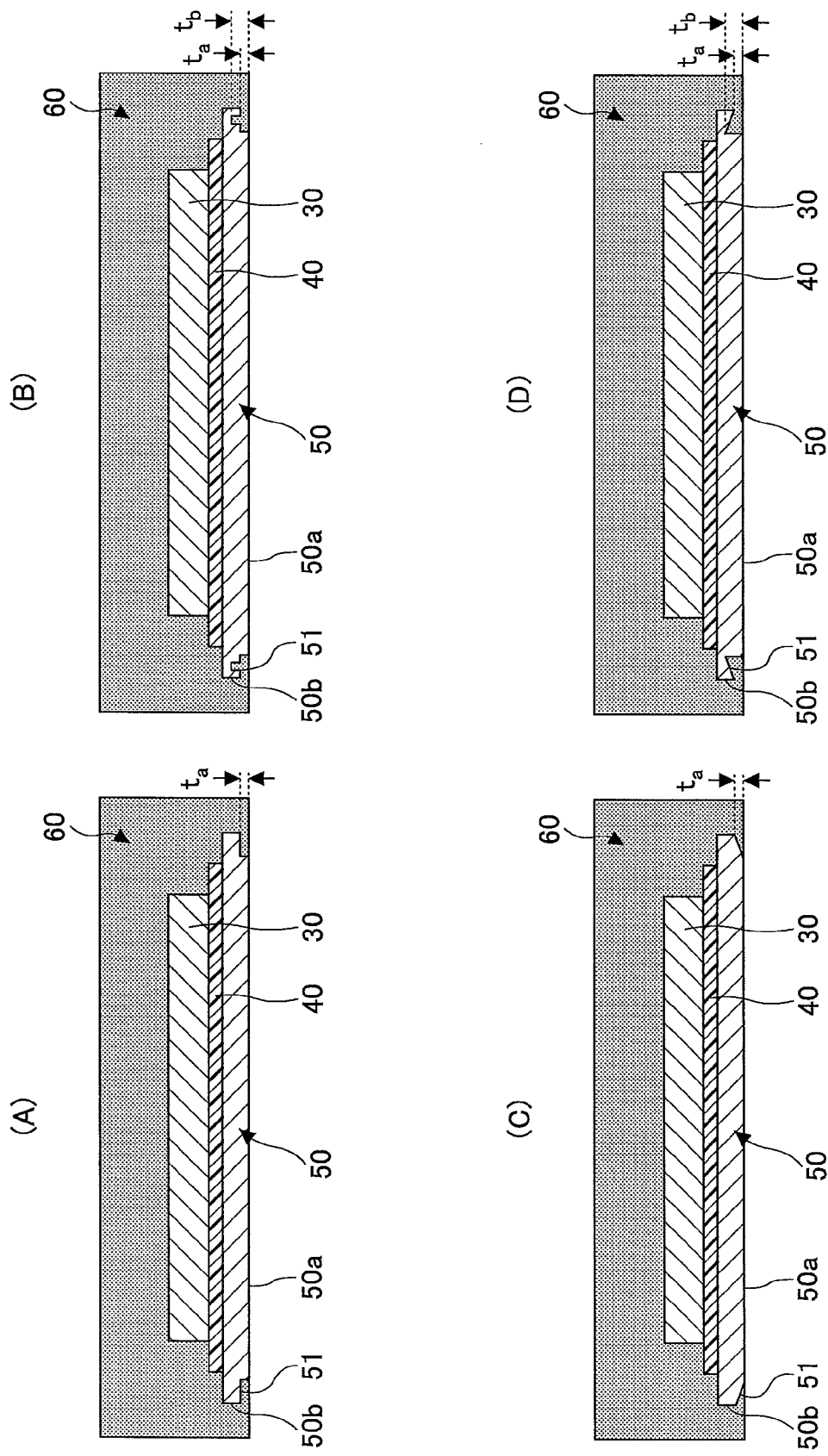
FIG. 5 is a diagram for illustrating preferred examples of an adhering manner between extended side portions 62 of a resin molded portion 60 and a side surface 50b of a metal plate portion.

FIG. 5 is a diagram for illustrating preferred examples of an adhering manner between the extended side portions 62 of the resin molded portion 60 and the side surface 50b of the metal plate portion 50. It is noted that hatching for the resin molded portion 60 is different from that in other drawings for visibility. It is noted that FIG. 5 shows a cross-sectional view corresponding to (B) in FIG. 3.

Thin portions 51 may be formed in the lower surface 50c of the metal plate portion 50 so as to further increase adhesion between the side surface 50b of the metal plate portion 50 and the extended side portions 62 of the resin molded portion 60, as illustrated in FIG. 5. The thin portions 51 are formed on the side opposed to the side surface 50b in the lower surface 50c of the metal plate portion 50. In other words, the thin portions 51 are formed by thinning the lower surface 50c of the metal plate portion 50 at the ends of the metal plate portion 50. The extended side portions of the resin molded portion 60 cover the lower surface 50c of the metal plate portion 50 at the thin portions 51 thereof. Regions of the extended side portions 62, which cover the lower surface 50c of the metal plate portion 50 at the thin portions 51, have thickness set such that they are substantially coplanar with the lower surface 50c of the metal plate portion 50 on the center side.

The thin portions 51 are provided for a region in the side surface 50b of the metal plate portion 50 on which the extended side portions 62 are provided. In other words, the thin portions 51 are provided for the side surface 50b of the metal plate portion 50 except for the locations of the fastening portions 52 of the metal plate portion 50 where the extended side portions 62 don't exist. Preferably, the thin portions 51 are provided for the substantially overall side surface 50b of the metal plate portion 50 except for the locations of the fastening portions 52 of the metal plate portion 50, as is the case with the extended side portions 62. The thin portions 51 may be formed by any methods such as etching, pressing, machining, and a shape of a die for die casting, etc.

Specifically, according to the example in (A) in FIG. 5, the thin portions 51 are formed by reducing a constant thickness to from the lower surface 50a at the end of the metal plate portion 50.

According to the example in (B) in FIG. 5, the thin portions 51 are formed by reducing a varied thickness from the lower surface 50a at the end of the metal plate portion 50. The thickness to be reduced varies from a first thickness ta to the thickness ta via a second thickness tb which is greater than ta, when viewed from the edge of the end of the metal plate portion 50 to the center side. It is noted that in an alternative embodiment, the thickness to be reduced may vary from a first thickness ta to a third thickness (which is thinner than a thickness of the metal plate portion 50 and greater than or equal to 0) via a second thickness tb which is greater than ta.

According to the example in (C) in FIG. 5, the thin portions 51 are formed by reducing a varied thickness from the lower surface 50a at the end of the metal plate portion 50. The thickness to be reduced varies gradually from the first thickness ta to 0 when viewed from the edge of the end of the metal plate portion 50 to the center side. It is noted that in an alternative embodiment, the thickness to be reduced may gradually vary from the first thickness ta to a fourth thickness (which is thinner than the first thickness ta and greater than or equal to 0).

According to the example in (D) in FIG. 5, the thin portions 51 are formed by reducing a varied thickness from the lower surface 50a at the end of the metal plate portion 50. The thickness to be reduced varies gradually from the first thickness ta to the second thickness tb which is greater than ta, when viewed from the edge of the end of the metal plate portion 50 to the center side.

In the examples illustrated in FIG. 5, since the extended side portions 62 of the resin molded portion 60 extend to the side of the lower surface 50a of the metal plate portion 50 at the thin portions 51 (i.e., the extended side portions 62 cover the thin portions 51 from the lower side), the extended side portions 62 can adhere to the ends of the metal plate portion 50 such that they encompass the ends of the metal plate portion 50 from upper and lower sides, which increases adhesion between the resin molded portion 60 and the metal plate portion 50. It is noted that the examples in FIG. 5 are just representative examples. Further, the examples in FIG. 5 may be combined in any manner. The thin portions 51 may have any shape, as long as the extended side portions 62 can extend from the side surface 50b to the lower surface 50a of the metal plate portion 50 such that they are coplanar with the lower surface 50a of the metal plate portion 50 on the center side.

Figure 6:
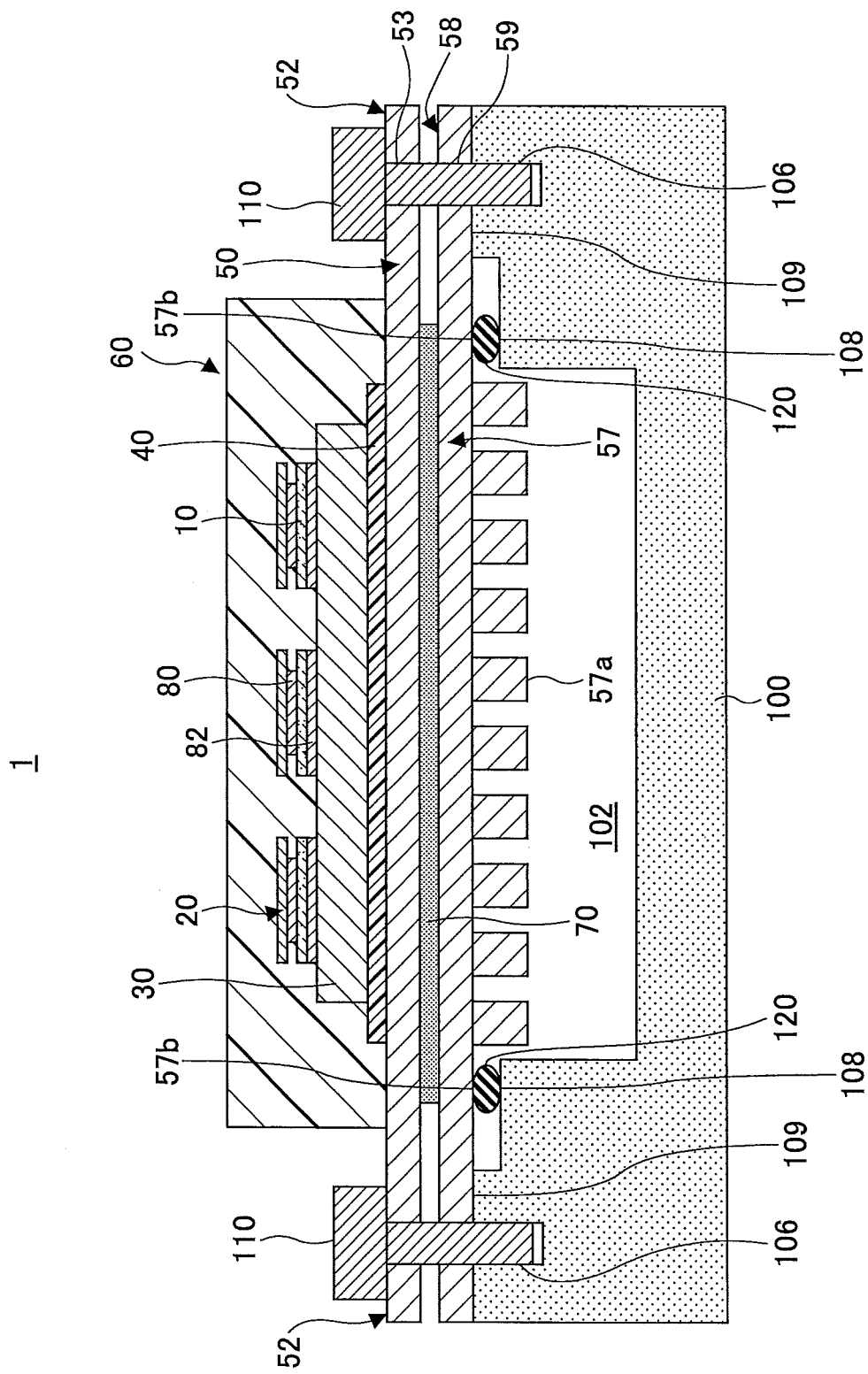
FIG. 6 is a cross-sectional view of an example of an installed status of the semiconductor module 1.

FIG. 6 is a cross-sectional view of an example of an installed status of the semiconductor module 1. In FIG. 6, the installed status of the semiconductor modules 2 is shown in a cross-sectional view (corresponding to (A) in FIG. 3) along a line A-A in FIG. 1.

The semiconductor module 1 is bolted to a channel forming member (a water channel, a housing, etc.) 100 which forms a cooling media channel 102 through which cooling media (water in this example) is circulated, as illustrated in FIG. 6. Specifically, the semiconductor module 1 is coupled to the channel forming member 100 by means of bolts 110 in such an orientation that the side of the lower surface of the cooling plate portion 57, that is to say, the side of the fins 57a faces the cooling medium channel 102. For this reason, in the channel forming member 100 tapped holes 106 are formed at positions corresponding to fastening positions of the bolts 110 (i.e., positions of the mounting holes 53 and 59 of the fastening portions 52 and 58 of the metal plate portion 50 and the cooling plate portion 57). The bolts 110 are bolted into the corresponding tapped holes 106 of the channel forming member 100 via the corresponding mounting holes 53 and 59 of the fastening portions 52 and 58 of the metal plate portion 50 and the cooling plate portion 57. It is noted that the cooling medium channel 102 is defined by the channel forming member 100 in cooperation with the lower surface of the cooling plate portion 57, as illustrated in FIG. 6.

Further, between the lower surface of the cooling plate portion 57 and the channel forming member 100 a sealing member 120 is provided to seal between the lower surface of the cooling plate portion 57 and the channel forming member 100. In other words, the sealing member 120 is provided between a seal portion 108 of the channel forming member 100 and a seal portion 57b of the lower surface of the cooling plate portion 57 such that it prevents leakage of the cooling media from the cooling media channel 102 of the channel forming member 100. The seal portion 57b of the cooling plate portion 57 may be provided over the overall periphery of the outer peripheral portion of the cooling plate portion 57. However, another seal portion may be provided for the outlet or inlet of the cooling medium channel 102, if necessary. Similarly, the seal portion 108 of the channel forming member 100 is provided such that it is opposed to the seal portion 55b of the cooling plate portion 57. Preferably, the seal portion 57b and the seal portion 108 are set outwardly with respect to the side portion of the metal block 30 and are set on the center side with respect to the side portion of the resin molded portion 60. With this arrangement, it is possible to efficiently ensure the sealing area and downsize the semiconductor module 1 in the Y direction. Further, it is possible to prevent the resin molded portion 60 from being subjected to the cooling medium such as water. Further, it is possible to provide space between the fastening positions of the bolts 110 (i.e., the fastening portions 58) and the sealing area (the seal portion 57b), because the seal portion 57b is located on the center side of the cooling plate portion 57 with respect to the fastening positions of the bolts 110 (i.e., the fastening portions 58).

In the illustrated example, the seal portion 108 is formed in a step which is set downwardly from a support surface 109 for supporting the mounting portions 58 of the cooling plate portion 57. The sealing member 120 is disposed and elastically compressed in a space created by the step between the seal portion 57b of the cooling plate portion 57 and the seal portion 108. Typically, the sealing member 120 is a rubber packing whose cross section is substantially circular, for example. However, the sealing member 120 may be formed of any material with any cross section as long as it implements sealing between the seal portion 57b and the seal portion 108. The sealing member 120 may have a shape or an outline corresponding to the seal portion 57b and the seal portion 108. The sealing member 120 may have a ring-like shape corresponding to the outer peripheral portion of the cooling plate portion 57 if the seal portion 57b and the seal portion 108 are provided over the overall periphery of the outer peripheral portion of the cooling plate portion 57. It is noted that a relationship (such as a clearance) between the seal portion 57b and the seal portion 108 may be any as long as it implements necessary sealing between the seal portion 57b and the seal portion 108 in cooperation with the sealing member 120.

Figure 7:
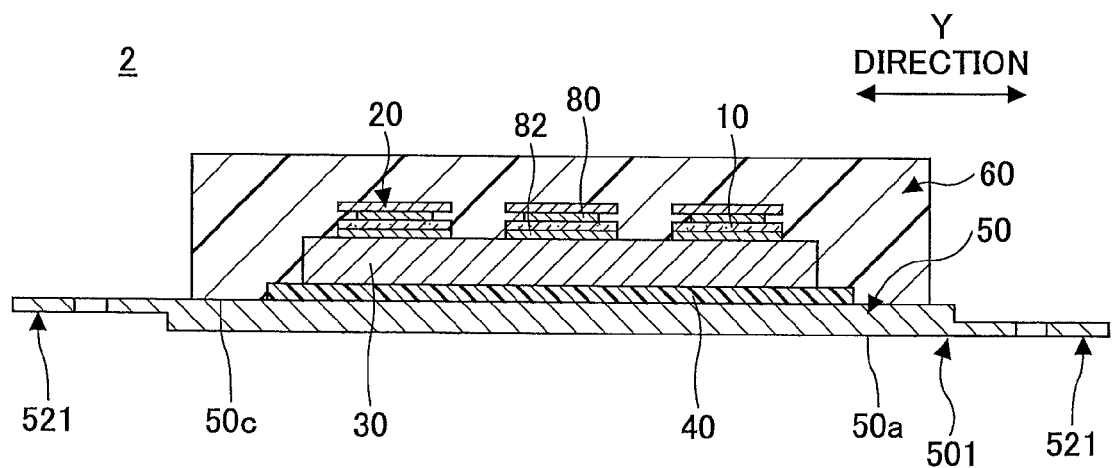
FIG. 7 is a diagram for illustrating a main cross-section of a semiconductor module 2 according to another embodiment (a second embodiment) of the present invention.

FIG. 7 is a cross-sectional view for illustrating a main cross-section of a semiconductor module 2 according to another embodiment (a second embodiment) of the present invention. FIG. 7 illustrates a cross-section cut by a line A-A in FIG. 1 (corresponding to the cross-section illustrated in FIG. 3 (A)). It is noted in FIG. 7 a status in which a cooling plate portion 57 is not attached is illustrated for the sake of convenience. The semiconductor module 2 according to the embodiment has features in a configuration of a metal plate portion 501. Other configurations may be the same as those in the semiconductor module 1 according to the first embodiment. In the following, a feature configuration of the metal plate portion 501 is mainly explained.

The metal plate portion 501 includes fastening portions 521 on the opposite sides thereof in a direction (Y direction in FIG. 1, in this example). A configuration of the fastening portions 521 may be the same as the fastening portions 52 of the metal plate portion 50 according to the first embodiment described above except for a feature of thickness described hereinafter. Further, preferably, the fastening portions 521 are configured symmetrically with respect to the X direction of the metal plate portion 501 except for a feature of thickness described hereinafter.

The fastening portions 521 of the metal plate portion 501 are formed to have a thickness smaller than a center portion (a portion on the center side with respect to the end; a portion except for the fastening portions 521 in the illustrated example) of the metal plate portion 501, as illustrated in FIG. 7. Preferably, the fastening portions 521 of the metal plate portion 501 have half of the thickness of the center portion of the metal plate portion 501. Further, the fastening portions 521 of the metal plate portion 501 at one end of the metal plate portion 501 in the Y direction (on the left side in the illustrated example) are formed to be coplanar with the upper surface 50c of the metal plate portion 501, while the fastening portions 521 of the metal plate portion 501 at another end of the metal plate portion 501 in the Y direction (on the right side in the illustrated example) are formed to be coplanar with the lower surface 50a of the metal plate portion 501. In other words, the fastening portions 521 of the metal plate portion 501 at one end of the metal plate portion 501 in the Y direction (on the left side in the illustrated example) are thinned on the side of the lower surface 50a of the metal plate portion 501, while the fastening portions 521 of the metal plate portion 501 at another end of the metal plate portion 501 in the Y direction (on the right side in the illustrated example) are thinned on the side of the upper surface 50c of the metal plate portion 501. At that time, the thinned thickness may be half of the thickness of the center portion of the metal plate portion 501.

Figure 8:
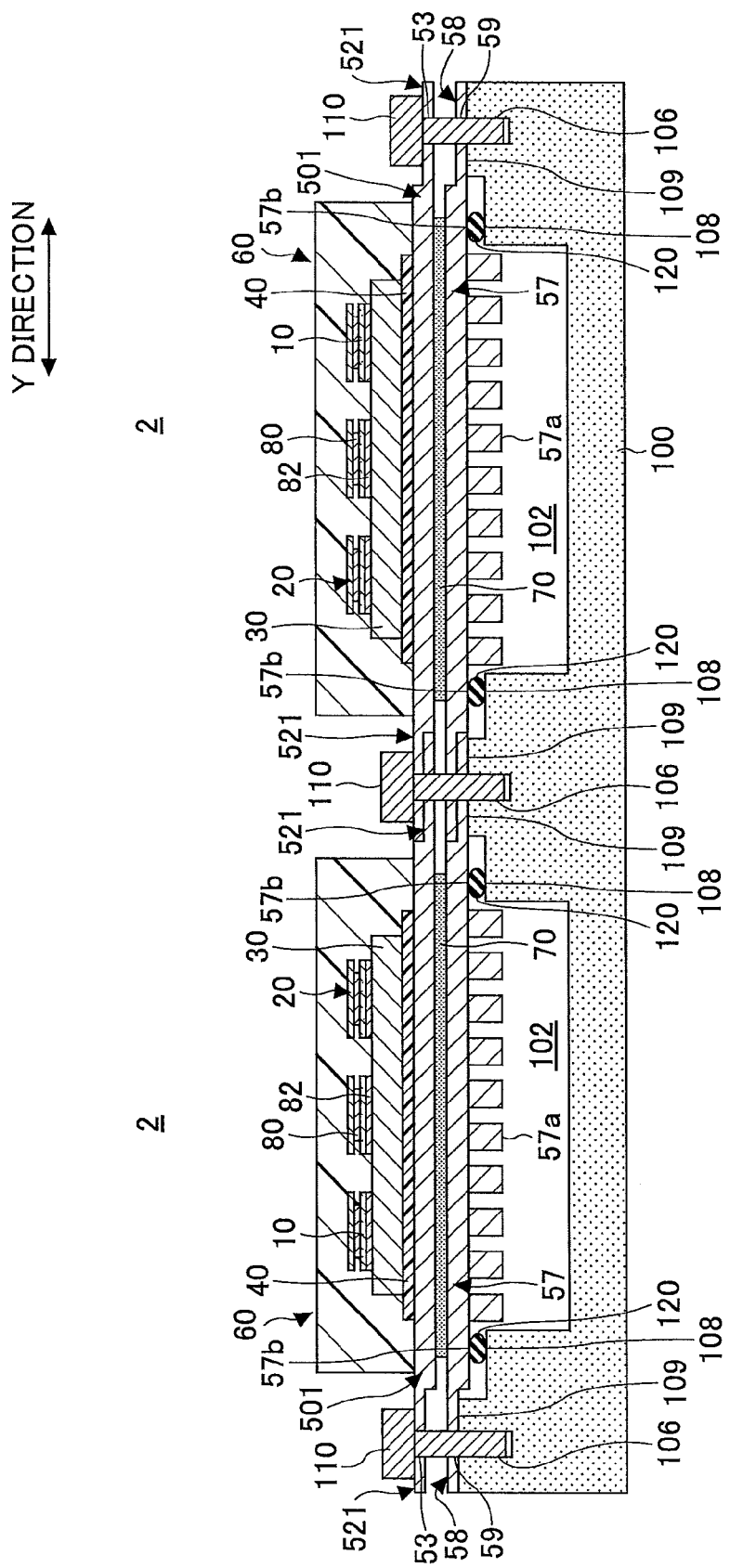
FIG. 8 is a cross-sectional view of an example of an installed status of two semiconductor modules 2.

FIG. 8 is a cross-sectional view of an example of an installed status of two semiconductor modules 2. In FIG. 8, the installed status of the semiconductor modules 2 is shown in a cross-sectional view (corresponding to (A) in FIG. 3) along a line A-A in FIG. 1.

It is preferred that two or more semiconductor modules 2 are installed to be arranged in the Y direction, as illustrated in FIG. 8. At that time, as illustrated in FIG. 8, the semiconductor modules 2 neighboring in the Y direction are simultaneously fastened by means of bolts 110 such that the fastening portions 521 of the metal plate portion 501 of one semiconductor module 2 are overlaid above or below the fastening portions 521 of the metal plate portion 501 of another semiconductor module 2. The respective semiconductor modules 2 are fastened to the channel forming member (a water channel, a housing, etc.) 100 by means of the bolts 110 which passes through the overlaid fastening portions 521 of the metal plate portions 501 of two neighboring semiconductor modules 2. It is noted that at that time the respective cooling plate portions 57 are fastened to a channel forming member together with the corresponding metal plate portions 501, as is the case with the embodiment illustrated in FIG. 6. It is noted that the cooling plate portion 57 may be formed by a large plate member which may be common to plural metal plate portions 501. In the example illustrated in FIG. 8, the cooling plate portions 57 also include the fastening portions 58 with the same thickness feature as the fastening portions 521 of the metal plate portion 501. The fastening portions of the cooling plate portions 57 are overlaid above or below the neighboring fastening portions 58 of the cooling plate portions 57 to be simultaneously fastened by means of bolts 110.

According to the semiconductor module 2 of the present embodiment, the following effects, among other things, can be obtained in addition to the effects obtained by the semiconductor module 1 according to the first embodiment described above. According to the semiconductor module 2 of the present embodiment, when two or more semiconductor modules 2 are installed to be arranged in the Y direction, the respective fastening portions 521 can be overlaid. With this arrangement, two or more semiconductor modules 2 can be effectively installed to be arranged in the Y direction, utilizing a space with a shorter distance in the Y direction. In other words, space-saving in the Y direction (a miniaturization of the whole module) can be implemented. Further, since the respective fastening portions 521 are overlaid to be fastened simultaneously, it is possible to reduce the number of the required bolts 110. It is noted that if the overlaid fastening portions 521 of the metal plate portions 501 of two neighboring semiconductor modules 2 are configured such that they have half of the thickness of the center portion of the metal plate portion 501, the fastening portions 521 of the metal plate portions 501 of one semiconductor module are coplanar with the upper surface 50c of the metal plate portion 501, and the fastening portions 521 of the metal plate portion 501 of another semiconductor module 2 are coplanar with the lower surface 50a of the metal plate portion 501, heights of the respective semiconductor modules 2 in the installed status may be the same.

It is noted that as described above it is preferred that two or more semiconductor modules 2 are installed to be arranged in the Y direction; however, each semiconductor module 3 may be fastened to the channel forming member (a water channel, a housing, etc.) 100 as is the case with the installed status of the semiconductor module 1 illustrated in FIG. 6.

Figure 9:
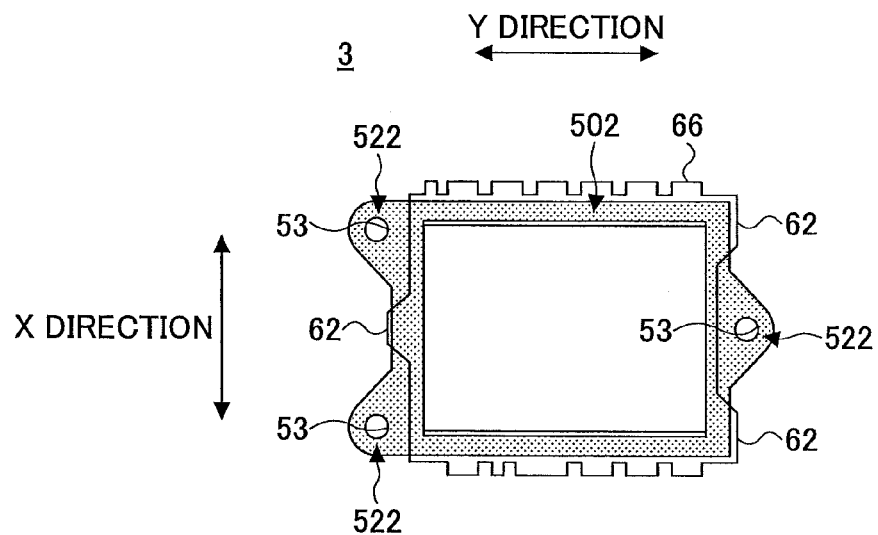
FIG. 9 is a plane view for illustrating a lower surface side of a semiconductor module 3 according to yet another embodiment (a third embodiment) of the present invention.

FIG. 9 is a plane view for illustrating a lower surface side of a semiconductor module 3 according to yet another embodiment (a third embodiment) of the present invention. It is noted in FIG. 9 a status in which a cooling plate portion is not attached is illustrated for the sake of convenience. The semiconductor module 3 according to the embodiment has features in a configuration of a metal plate portion 502. Other configurations may be the same as those in the semiconductor module 1 according to the first embodiment. In the following, a feature configuration of the metal plate portion 502 is mainly explained.

The metal plate portion 502 includes fastening portions 522 on the opposite sides thereof in a direction (Y direction in FIG. 1, in this example). The fastening portions 522 are formed in areas at the ends of the metal plate portion 502, which areas project in the Y direction with respect to their neighboring areas, as illustrated in FIG. 9. According to the present embodiment, two fastening portions 522 are formed at one end of the metal plate portion 502 in the Y direction (on the left side in the illustrated example) such that they are formed in areas located on opposite sides in the X direction, which areas project in the Y direction with respect to an area therebetween. In other words, a shape of one end of the metal plate portion 502 in the Y direction (on the left side in the illustrated example) is concave with the opposite projecting ends when viewed in the Y direction from the center side. The fastening portions 522 are set on the opposite ends in the X direction. Further, a single fastening portions 522 is formed at another end of the metal plate portion 502 in the Y direction (on the right side in the illustrated example) such that it is formed in a center area in the X direction which projects in the Y direction with respect to the opposite areas in the X direction. In other words, a shape of another end of the metal plate portion 502 in the Y direction (on the right side in the illustrated example) is convex with the projecting center area when viewed in the Y direction from the center side. The single fastening portion 522 is set on the center area in the X direction.

The side portion of the resin molded portion 60 in the Y direction is located on the center side with respect to the outermost position of the fastening portions 522 in the Y direction. In the illustrated example, the side portion of the resin molded portion 60 in the Y direction does not extend outwardly from the side surface 50b of the metal plate portion 502 except for the extended side portions 62. It is noted that in the illustrated example the extended side portions 62 in the convex-shaped end (the right end in FIG. 9) are formed on the opposite sides of the fastening portions 522 in the X direction.

It is noted that the cooling plate portion of the semiconductor module 3 includes the fastening portions 58 corresponding to the fastening portions 52 of the metal plate portion 502. The cooling plate portion 57 may have substantially the same outline as the metal plate portion 502.

Figure 10:
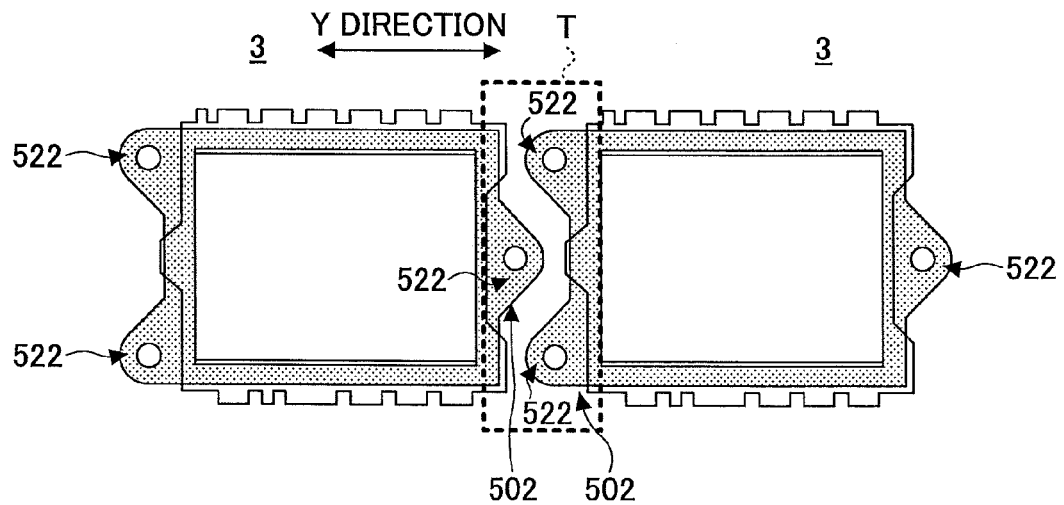
FIG. 10 is a plane view for illustrating an example of an installed status of two semiconductor module 3 viewed from a lower surface side of the semiconductor module 3.

FIG. 10 is a plane view for illustrating an example of an installed status of two semiconductor modules 3 viewed from a lower surface side of the semiconductor module 3. It is noted in FIG. 10 a status in which a cooling plate portion 57 is not attached is illustrated for the sake of convenience.

It is preferred that two or more semiconductor module 3 are installed to be arranged in the Y direction, as illustrated in FIG. 10. At that time, as illustrated in a dashed line region in FIG. 10, the semiconductor modules 3 neighboring in the Y direction are installed such that the fastening portion 522 at the convex-shaped end of the metal plate portion 502 of one semiconductor module 3 enters a center region (a concave region) of in the X direction at the concave end of the metal plate portion 502 of another semiconductor module 3. In other words, the semiconductor modules 3 neighboring in the Y direction are installed such that two fastening portions 522 of one semiconductor module 3 and a single fastening portion 522 of another semiconductor module 3 are opposed in the Y direction and shifted in the X direction (i.e., two fastening portions 522 of one semiconductor module 3 and a single fastening portion 522 of another semiconductor module 3 are overlapped in a complementary manner in the Y direction). It is noted that at that time the respective cooling plate portions 57 are fastened to a channel forming member together with the metal plate portions 502, as is the case with the embodiment illustrated in FIG. 6. It is noted that the cooling plate portion 57 may be formed by a large plate member which may be common to plural metal plate portions 502.

According to the semiconductor module 3 of the present embodiment, the following effects, among other things, can be obtained in addition to the effects obtained by the semiconductor module 1 according to the first embodiment described above. According to the semiconductor module 3 of the present embodiment, when two or more semiconductor modules 3 are installed to be arranged in the Y direction, the respective fastening portions 522 can be overlapped in a complementary manner in the Y direction. With this arrangement, two or more semiconductor modules 2 can be effectively installed to be arranged in the Y direction, utilizing a space with a shorter distance in the Y direction. In other words, space-saving in the Y direction (a miniaturization of the whole module) can be implemented.

It is noted that in the third embodiment the relationship between the fastening portion 522 at one end and the fastening portions 522 at another end of the metal plate portion 502 is not limited to the example described above. As long as the fastening portion 522 at one end and the fastening portions 522 at another end of the metal plate portion 502 are offset with respect to each other in the X direction, the effects described above can be obtained. Further, the number of the fastening portions 522 at one end of the metal plate portion 502 may be an arbitrary number as needed. The number of the fastening portions 522 may be the same or different between the opposite ends of the metal plate portion 502.

It is noted that as described above it is preferred that two or more semiconductor modules 3 are installed to be arranged in the Y direction; however, each semiconductor module 3 may be fastened to the channel forming member 100 as is the case with the installed status of the semiconductor module 1 illustrated in FIG. 6.

Figure 11:
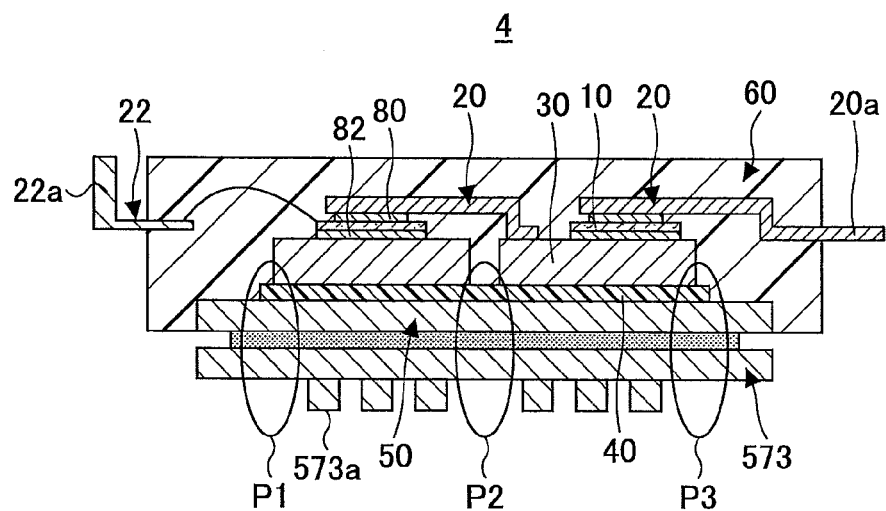
FIG. 11 is a diagram for illustrating a main cross-section of a semiconductor module 4 according to another embodiment (a fourth embodiment) of the present invention.
Figure 12:
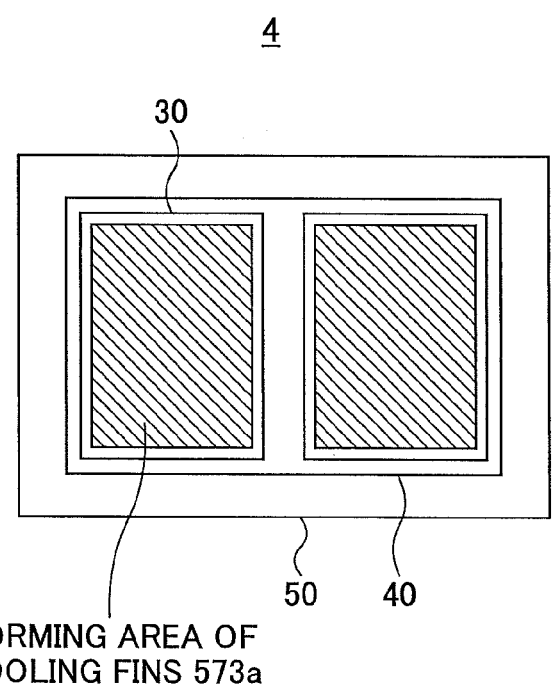
FIG. 12 is a projection view of the semiconductor module 4 viewed from the lower side.

FIG. 11 is a cross-sectional view for illustrating a main cross-section of a semiconductor module 4 according to another embodiment (a fourth embodiment) of the present invention. FIG. 11 illustrates a cross-section cut by a line C-C in FIG. 1 (corresponding to the cross-section illustrated in FIG. 3 (C)). FIG. 12 is a projection view of the semiconductor module 4 viewed from the lower side. FIG. 12 illustrates a forming region of fins 573a. The semiconductor module 4 according to the embodiment has features in a configuration of a cooling plate portion 573. Other configurations may be the same as those in the semiconductor module 1 according to the first embodiment described above. For example, fastening portions of the cooling plate portion 573 (not illustrated) may be the same as the fastening portions 58 of the cooling plate portion 57 according to the first embodiment described above. In the following, a feature configuration of the cooling plate portion 573 is mainly explained.

The configuration of the cooling plate portion 573 may be substantially the same as the configuration of cooling plate portion 57 according to the first embodiment described above except for the forming region of fins 573a. The fins 573a are formed on the center side with respect to the side portions of the metal blocks 30, as illustrated in FIG. 11 and FIG. 12. In other words, the fins 573a are formed such that in the projection view the side portions of the metal blocks 30 extends outwardly with respect to the forming region of fins 573a.

According to the semiconductor module 4 of the present embodiment, the following effects, among other things, can be obtained in addition to the effects obtained by the semiconductor module 1 according to the first embodiment described above. According to the semiconductor module 4 of the present embodiment, since in the projection view the side portions of the metal blocks 30 extends outwardly with respect to the forming region of fins 573a, an inspection (an ultrasonic inspection or the like, for example) of the semiconductor module 4 can be performed more easily. Specifically, when the inside (bonded statuses between the respective components inside the resin molded portion 60, etc.) of the semiconductor module 4 is inspected with ultrasonic test equipment, ultrasonic waves need to be radiated from the side of the lower surface of the semiconductor module 4; however, if there are fins 573a on the lower surface of the semiconductor module 4, ultrasonic waves may reflect at the fins 573a, and thus precise inspection results cannot be obtained. In contrast, according to the semiconductor module 4 of the present embodiment, it is possible to perform the ultrasonic inspection of the semiconductor module 4 with high accuracy without removing the cooling plate portion 573 by utilizing areas P1, P2 and P3 (see FIG. 11) where the fins 573a are not formed. It is noted that the concrete inspection target may include the presence or absence of exfoliation (debonding) between the metal blocks 30 and the insulating sheet 40, the presence or absence of exfoliation between the insulating sheet 40 and the metal plate portion 50, etc.

Figure 13:
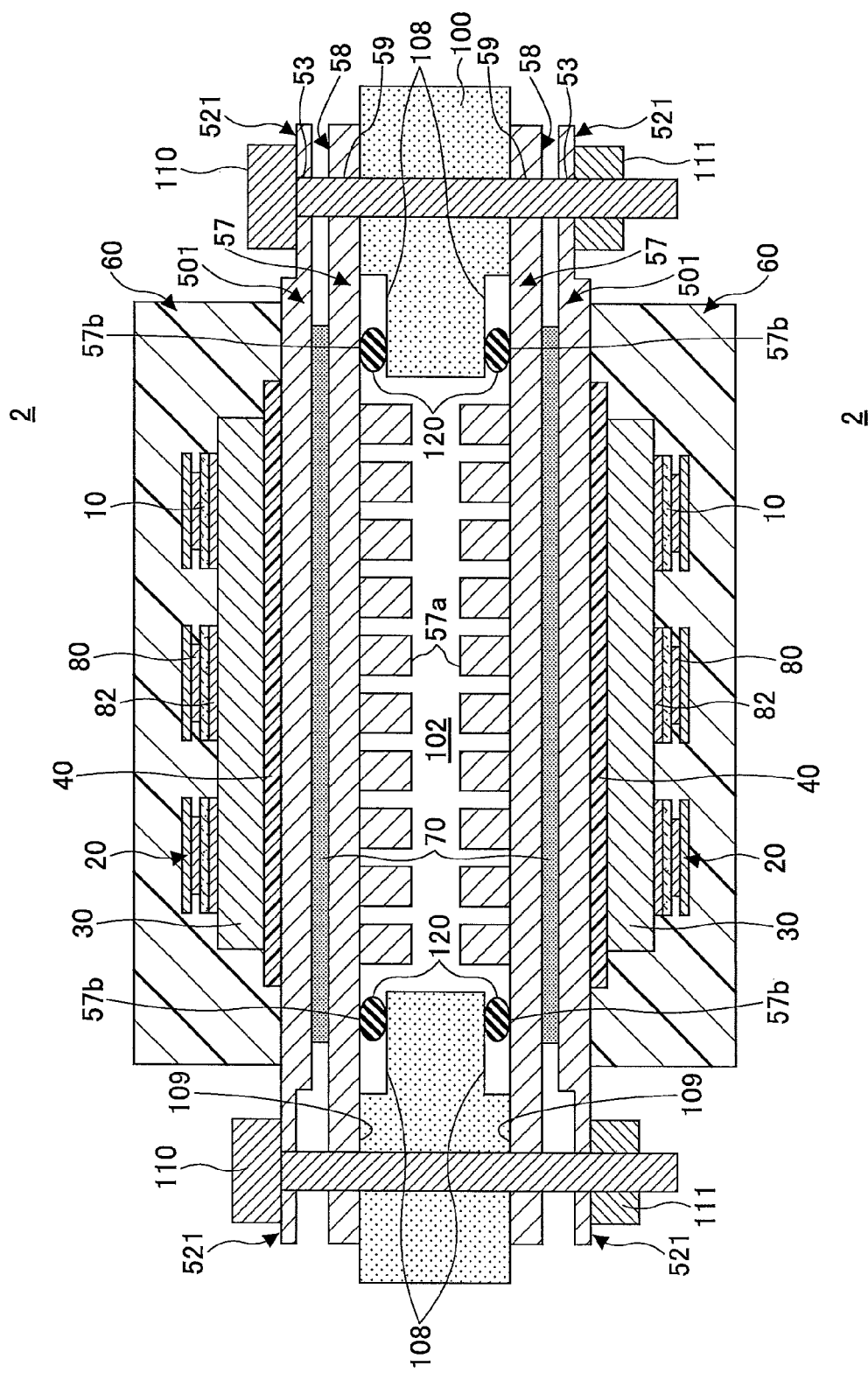
FIG. 13 is a cross-sectional view of an example of an installed status of two semiconductor module 2 which can be similarly applied to the respective embodiments.

FIG. 13 is a cross-sectional view of an example of an installed status of two semiconductor modules 2 which can be similarly applied to the respective embodiments described above. In FIG. 13, as an example, two semiconductor modules are used. In FIG. 13, the installed status of the semiconductor modules 2 is shown in a cross-sectional view (corresponding to (A) in FIG. 3) along a line A-A in FIG. 1.

The semiconductor modules 2 may be installed such that the sides where the fins 57a are formed are opposed to each other in a vertical direction, as illustrated in FIG. 13. In this case, as illustrated in FIG. 13, the upper and lower semiconductor modules 2 are fastened to the channel forming member (a water channel, a housing, etc.) 100 by means of common bolts 110 and nuts 111. In other words, the upper and lower semiconductor modules 2 are fastened to the channel forming member 100 by using the common bolts 110 and the common nuts 111 for the opposed fastening portions 521 of the metal plate portions 501 of the upper and lower semiconductor modules 2. It is noted that at that time the respective cooling plate portions 57 are fastened to a channel forming member together with the metal plate portions 50, as is the case with the embodiment illustrated in FIG. 6. With this arrangement, it is possible to reduce the number of the bolts 110, etc., required for the fastening. It is noted that if the semiconductor modules 2 are installed such that the sides where the fins 57a are formed are opposed to each other in a vertical direction as illustrated in FIG. 13, the cooling media channel 102 is defined by the cooling plate portion 57 (the surface on which the fins 57a are formed) in the vertical direction.

Next, with reference to FIG. 14 through FIG. 18, a feature configuration for increasing ease of performing an ultrasonic inspection with ultrasonic test equipment is described. Here, for the sake of convenience, explanation is made as to the semiconductor module 1 according to the first embodiment described above; however, it can be similarly applied to other second, third and fourth embodiments described above.

Figure 14:
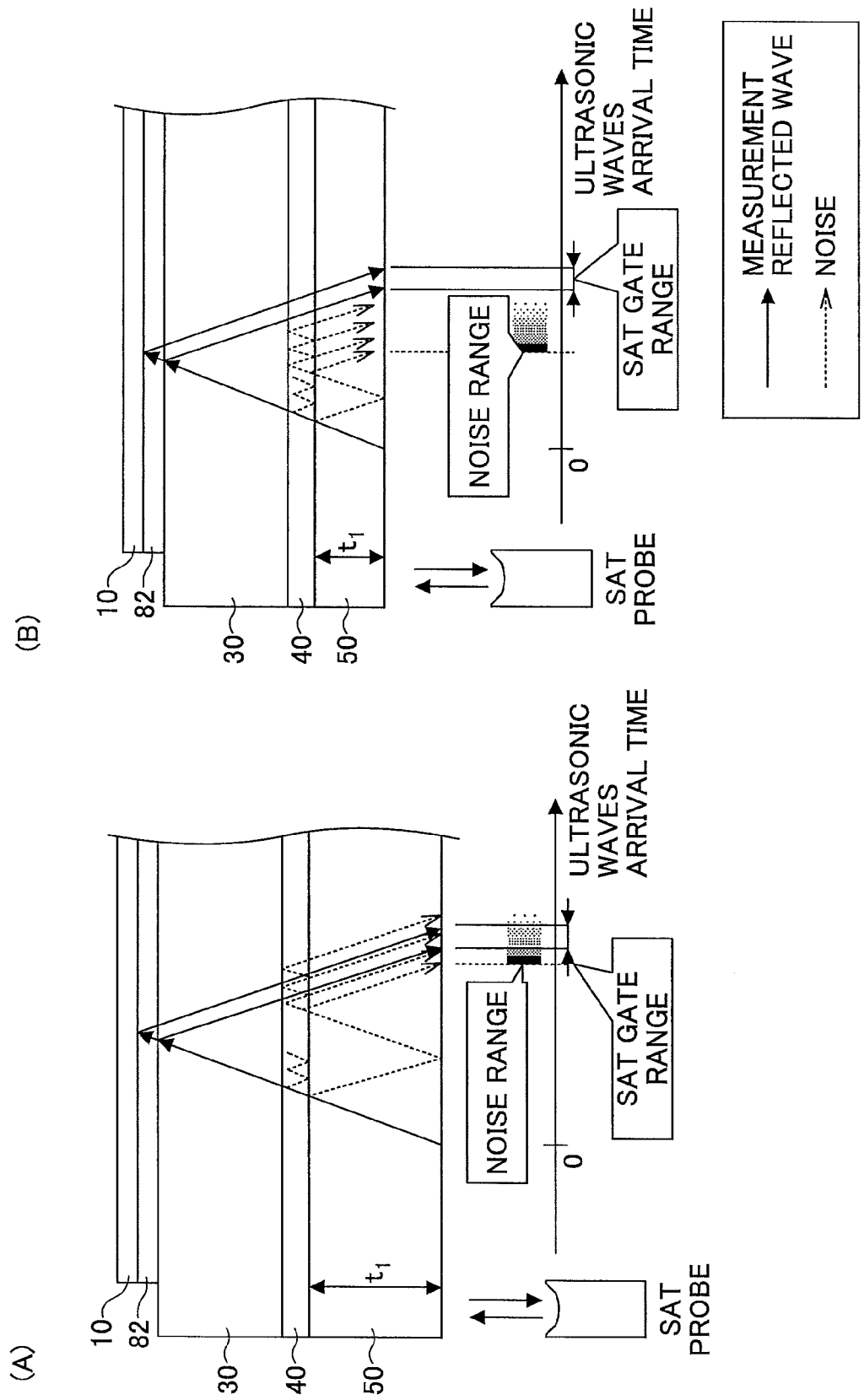
FIG. 14 is a diagram for schematically illustrating a relationship between a thickness of the metal plate portion 50 and a degree of ease (accuracy) of an ultrasonic inspection.

FIG. 14 is a diagram for schematically illustrating a relationship between a thickness of the metal plate portion 50 and a degree of ease (accuracy) of an ultrasonic inspection. Here, the semiconductor module 1 has the cooling plate portion 57 removed therefrom as described above and the side of the metal plate portion 50 is sunk in water. The inspection is performed by radiating the ultrasonic waves to the lower surface of the metal plate portion 50 from a probe (a SAT probe) of the ultrasonic test equipment and then analyzing the reflected waves. Further, in this example, the inspection target includes at least one of the presence or absence of exfoliation between the semiconductor devices 10 and the solder layers 82, the presence or absence of voids inside the solder layers 82, and the presence or absence of exfoliation between the solder layers 82 and the metal blocks 30. For this purpose, the ultrasonic waves to be measured are as follows, as illustrated by solid lines in FIG. 14.

(1) A reflected wave (referred to as a first measurement reflected wave) which reaches a boundary between the solder layers 82 and the metal blocks 30 without reflection and is reflected at the boundary between the solder layers 82 and the metal blocks 30 to return directly.

(2) A reflected wave (referred to as a second measurement reflected wave) which reaches a boundary between the semiconductor devices 10 and the solder layers 82 without reflection and is reflected at the boundary between the semiconductor devices 10 and the solder layers 82 to return directly.

Accordingly, a gate range of the ultrasonic test equipment (i.e., a monitoring range related to an ultrasonic wave arrival time) is set based on an arrival time of the first measurement reflected wave and an arrival time of the second measurement reflected wave. The gate range may be from the arrival time of the first measurement reflected wave to the arrival time of the second measurement reflected wave and plus alpha. The alpha is typically a time corresponding to one wavelength (for example, one wavelength in water), but it may be longer than the time corresponding to the one wavelength.

In FIG. 14, the thickness t1 of the metal plate portion 50 is different between the example illustrated in (A) and example illustrated in (B). In the example illustrated in FIG. 14 (A), many internal echo components (i.e., noise) are mixed in the gate range, and thus the measurement reflected waves are hidden by the internal echo components. The internal echo components includes reflected components which returns after repeating the reflection in the metal plate portion 50 and the insulating sheet 40 (i.e., reflected at the boundary between the metal blocks 30 and the insulating sheet 40, the boundary between the insulating sheet 40 and the metal plate portion 50, and the boundary between the metal plate portion 50 and the outside (water, for example)), as illustrated in FIG. 14. On the other hand, in the example illustrated in FIG. 14 (B), the internal echo components (i.e., noise) are not substantially mixed in the gate range, and thus the measurement reflected waves can be extracted with high accuracy by separating them from the internal echo components.

Thus, the thickness t1 of the metal plate portion 50 is set such that the internal echo component, which returns after reflecting the boundary between the metal blocks 30 and the insulating sheet 40, the internal echo component, which returns after reflecting the boundary the insulating sheet 40 and the metal plate portion 50, etc., are not substantially superposed in the gate range. With this arrangement, it becomes possible to separate the measurement reflected waves from the internal echo components to extract the measurement reflected waves with high accuracy, thereby increasing inspection accuracy.

Figure 15:
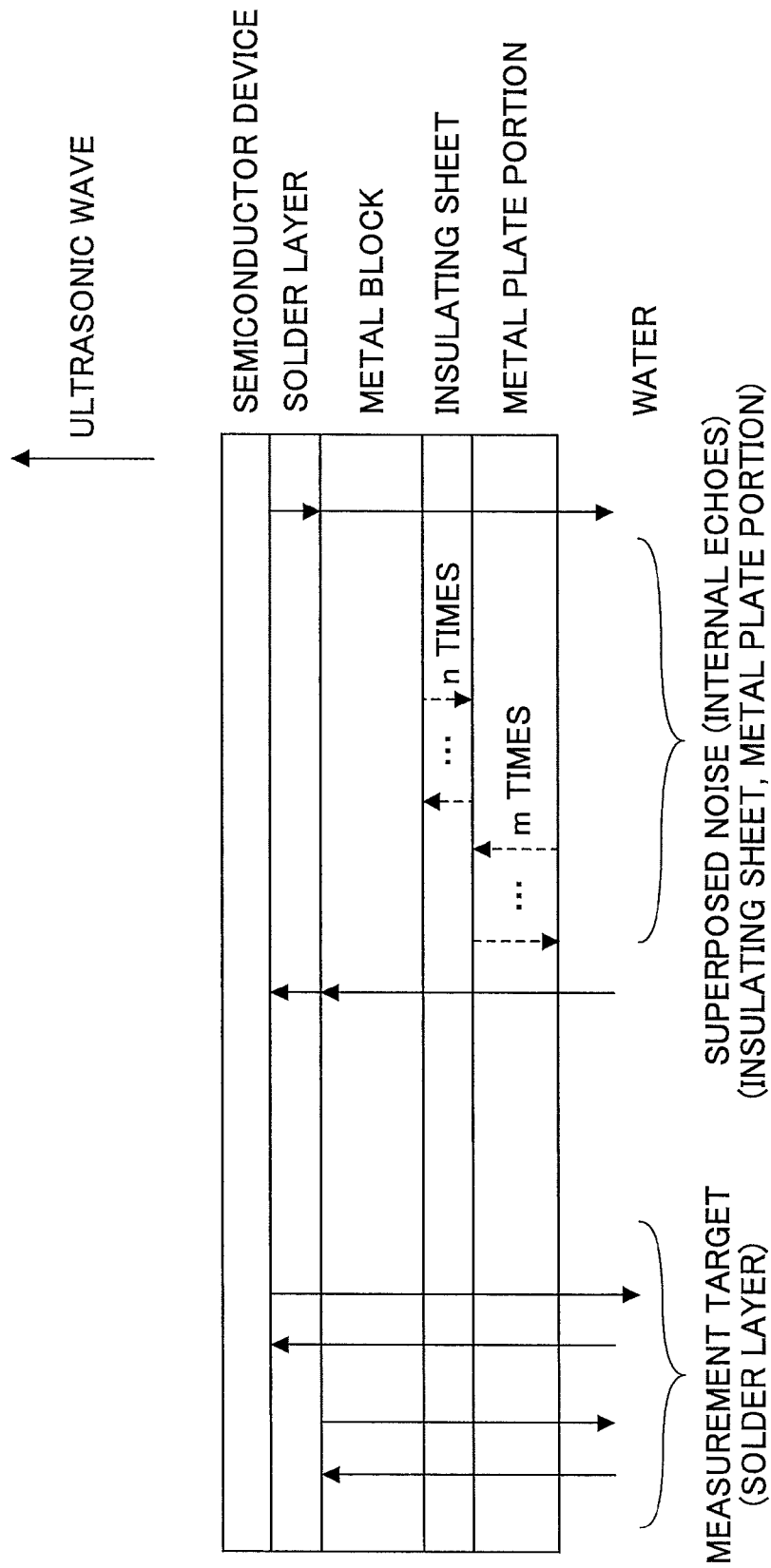
FIG. 15 is a diagram for explaining a way of deriving an appropriate range of a thickness t1 of the metal plate portion 50.

Here, with reference to FIG. 15, etc., an example of a way of deriving an appropriate range of the thickness t1 of the metal plate portion 50 is described. Here, it is assumed that the internal echo components include the reflected wave which has m times of the round trip in the metal plate portion 50, and the reflected wave which has n times of the round trip in the insulating sheet 40, as illustrated in FIG. 15.

The definition of the numerical subscripts used in the following formulas is as represented in FIG. 16. For example, the numerical subscript i=3 represents the layer of the metal blocks 30.

[1. Arrival Time of Measurement Reflected Wave]

The first measurement reflected wave (i.e., the reflected wave which returns directly after reflecting at the boundary between the solder layers 82 and the metal blocks 30) is as follows.

$$2\sum_{i=0}^{3} t_i/c_i$$

The second measurement reflected wave (i.e., the reflected wave which returns directly after reflecting at the boundary between the semiconductor devices 10 and the solder layers 82) is as follows.

$$2\sum_{i=0}^{4} t_i/c_i$$

At that time, the gate range Tg has one wavelength added at the end side as follows.

$$2\sum_{i=0}^{3} t_i/c_i \leq Tg \leq 2\sum_{i=0}^{4} t_i/c_i + 1/f$$

[2. Arrival Time of Internal Echo Components]

The arrival time Tmn of the internal echo component is expressed using the number of attenuation of the transmitted wave k as follows.

$$T_{mn} = 2\{t_0/c_0 + m \cdot t_1/c_1 + n \cdot t_2/c_2\} + k/f$$

[3. Determination of m]

Initial m (an integer equal to or greater than 2) which meets the relationship $Tg < T_{(m+1)0}$ is derived from the following equation.

$$2\sum_{i=0}^{4} t_i/c_i + 1/f < 2\{t_0/c_0 + (m+1) \cdot t_1/c_1 + 0 \cdot t_2/c_2\} + k/f$$

Thus, m (an integer equal to or greater than 2) is an integer which meets the following relationship.

$$m - 1 < \frac{1}{2} \cdot c_1/t_1 \left\{ 2\sum_{i=0}^{4} t_i/c_i + \frac{(1-k)}{f} \right\} < m \qquad \text{Formula (1)}$$

[4. Determination of overlapped range (determination of appropriate thickness t1)]

Here it is assumed that the thickness of the insulating sheet 40 is thin and the measurement of the measurement reflected waves is not possible before $T_{m0} \sim T_{m(n_{max})}$ because waves are crowded densely and the internal echo components are superposed. Based on the assumption, if these following two conditions (i.e., formulas (2) and (3)) are met, it is possible to measure the measurement reflected waves because the internal echo components are not superposed.

$$T_{m(n_{max})} < Tg \qquad \text{Formula (2)}$$

$$Tg < T_{(m+1)0} \qquad \text{Formula (3)}$$

The formula (2) can be expressed as follows.

$$2\{t_0/c_0 + m \cdot t_1/c_1 + n_{max} \cdot t_2/c_2\} + k/f < 2\sum_{i=0}^{3} t_i/c_i$$

This formula can be organized to be expressed as follows.

$$\frac{(m-1) \cdot t_1}{c_1} < \sum_{i=2}^{3} t_i/c_i - \frac{k}{2f} - n_{max} \cdot t_2/c_2 \qquad \text{Formula (2')}$$

The formula (3) can be expressed as follows.

$$2\sum_{i=0}^{4} t_i/c_i + 1/f < 2\{t_0/c_0 + (m+1) \cdot t_1/c_1 + 0 \cdot t_2/c_2\} + k/f$$

This formula can be organized to be expressed as follows.

$$\frac{m \cdot t_1}{c_1} < \sum_{i=2}^{3} t_i/c_i - \frac{k}{2f} + \frac{t_4}{c_4} + \frac{1}{2f} \qquad \text{Formula (3')}$$

Thus, by determining t1 which meets the formulas (1), (2') and (3') as described above, it is possible to derive an appropriate range of the thickness t1. Specifically, by determining m from the formula (1) and then using m to determine t1 which meets the formulas (2') and (3') as described above, it is possible to derive an appropriate range of the thickness t1.

Next, an example of calculation is described in which an appropriate range of the thickness t1 is derived under a particular condition. Here, the conditions illustrated in FIG. 17 are used. It is noted that the metal blocks 30 are formed from copper, the insulating sheet 40 is formed from a resin, and the metal plate portion 50 is formed from aluminum. Further, a mark "–" in FIG. 17 indicates that the variable in the question is arbitrary. It is noted that in the calculation it is assumed that a frequency is 50 MHz, the number of attenuation is (times) and $n_{max}$ is 4 (times).

Figure 18:
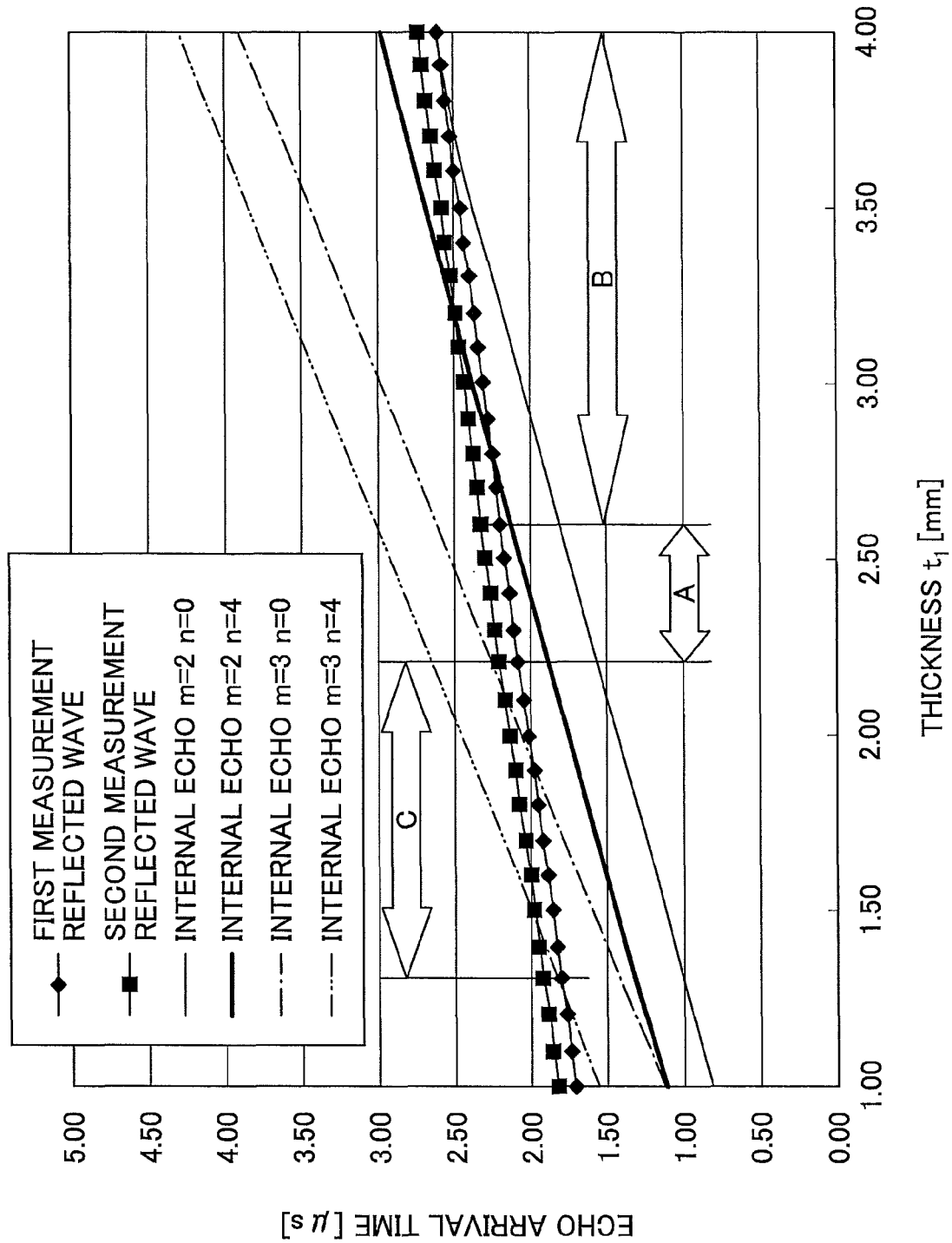
FIG. 18 is a graph for illustrating a calculation result of the appropriate range of a thickness t1 of the metal plate portion 50.

FIG. 18 illustrates a graph of the calculation results. In FIG. 18, change manners of respective parameters when the thickness t1 varies in a range from 1 to 4 [mm] are illustrated. The parameters are the first measurement reflected wave (i.e., the reflected wave which returns directly after reflecting at the boundary between the solder layers 82 and the metal blocks 30), the second measurement reflected wave (i.e., the reflected wave which returns directly after reflecting at the boundary between the semiconductor devices 10 and the solder layers 82), and the arrival times of the internal echo components. The arrival times of the internal echo components are illustrated with respect to four cases (m, n)=(2, 0), (2, 4), (3, 0) and (3, 4).

When it is assumed that the range of the thickness t1 of the metal plate portion 50 is from 1 to 4 [mm], m which meets the formula (1) described above in this range of the thickness t1 is "2", and thus an appropriate range of the thickness t1 is from about 2.3 to about 2.5 [mm]. Specifically, as illustrated in FIG. 18, with respect to a section A in which the range of the thickness t1 is from about 2.3 to about 2.5 [mm], since the arrival time of the first measurement reflected wave and the arrival time of the second measurement reflected wave are well deviated from the arrival times of the internal echo components (i.e., the internal echo components are not superposed on the first measurement reflected wave and the second measurement reflected wave), the first measurement reflected wave and the second measurement reflected wave can be measured with high accuracy. In contrast, if the thickness t1 of the metal plate portion 50 falls in another section B or C, since the internal echo components are not superposed on the first measurement reflected wave and the second measurement reflected wave, it is difficult to measure the first measurement reflected wave and the second measurement reflected wave with high accuracy.

Figure 19:
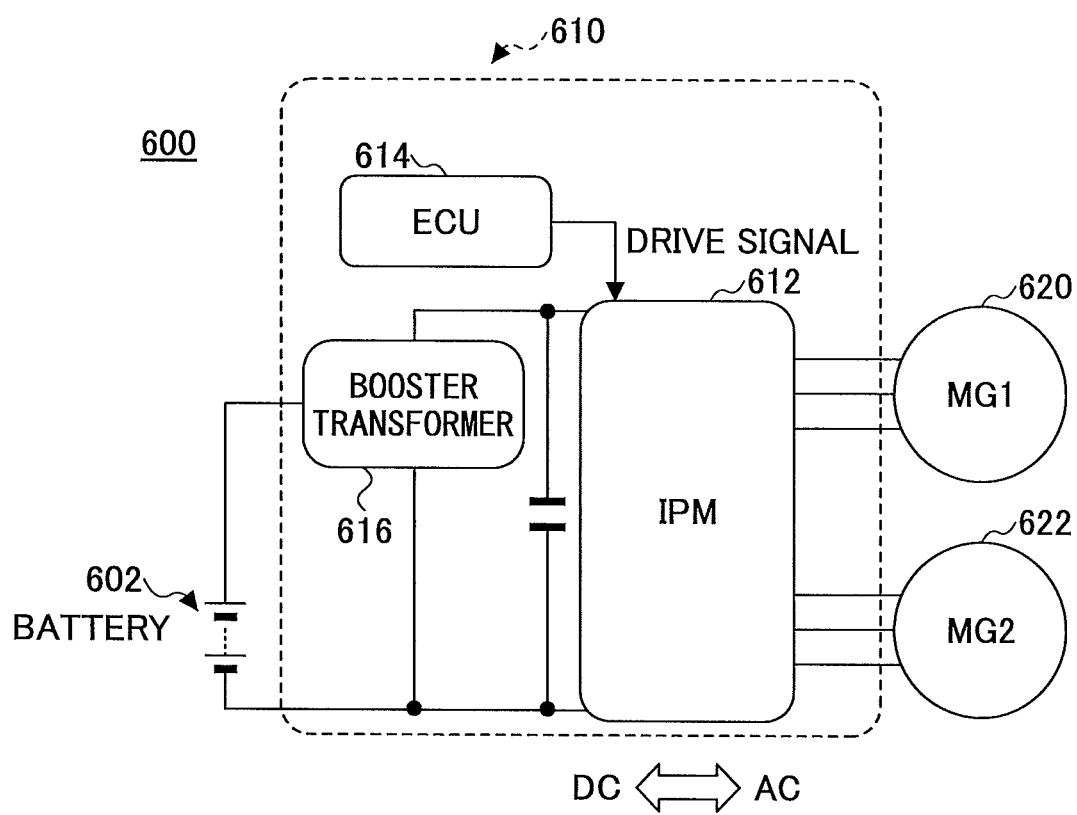
FIG. 19 is a diagram for schematically illustrating an example of a hybrid system 600 including the semiconductor module 1, 2, etc., according to the respective embodiments.

FIG. 19 is a diagram for schematically illustrating an example of a hybrid system 600 including the semiconductor module 1, 2, etc., according to the respective embodiments described above.

In the illustrated embodiment, the hybrid system 600 includes a battery 602, an inverter 610, and motor generators 620, 622. The semiconductor module 1, 2, etc., according to the respective embodiments described above may be implemented as an IPM (Intelligent Power Module) 612. The IPM 612 is installed in the inverter 610 and performs the transformation between direct current (DC) and alternating current (AC) by means of PWM control based on signals supplied from an ECU 614. It is noted that in the illustrated embodiment a DC-DC booster transformer 616 is added in the inverter 610.

The present invention is disclosed with reference to the preferred embodiments. However, it should be understood that the present invention is not limited to the above-described embodiments, and variations and modifications may be made without departing from the scope of the present invention.

For example, in the above-described embodiments, the semiconductor devices 10 are configured with a total of six arms of upper arms and lower arms wherein each arm includes U-phase, V-phase and W-phase. However, the number of the arms installed in the semiconductor module 1 may be any. If the semiconductor module 1 is embodied as an inverter for driving two motors (see FIG. 19), for example, the semiconductor devices 10 may be configured with the respective arm of the upper and lower arms of U-phase, V-phase and W-phase for the first motor and the respective arm of the upper and lower arms of U-phase, V-phase and W-phase for the second motor. Further, several semiconductor devices 10 may be installed in parallel for one arm.

Further, the semiconductor module 1 may include another configuration (parts of elements of a DC-DC booster transformer for driving a motor, for example), and the semiconductor module 1 may include another element (capacitor, inductor, etc.) in addition to the semiconductor devices 10. Further, the semiconductor module 1 may be any module as long as it requires cooling, and thus is not limited to the semiconductor module which implements the inverter. Further, the semiconductor module 1 may be implemented as an inverter used for applications (a train, an air conditioner, an elevator, a refrigerator, etc.) other than vehicle applications.

Further, in the above-described first embodiment, if the semiconductor modules 1 are arranged in the Y direction, the semiconductor modules 1 may be arranged in a staggered configuration such that two neighboring semiconductor modules 1 are offset to each other in the X direction. In other words, the semiconductor modules 1 may be arranged in the Y direction such that one of the mounting portions 52 of one of the two neighboring semiconductor modules 1 is included in space (concave area in the end in the Y direction) between the mounting portions 52 of the other of the two neighboring semiconductor modules 1. In this case, when more than two semiconductor modules 1 are installed such that they are aligned in the Y direction as is the case with the installed status of the semiconductor module 3 illustrated in FIG. 10, it is possible to efficiently install them by utilizing reduced space in the Y direction. Thus, it is possible to save space in the Y direction (and thus downsize the module as a whole).

DESCRIPTION OF REFERENCE SYMBOLS 1,2,3,4 semiconductor module
10 semiconductor device
20 wiring member
20a terminal portion
22 wiring member
22a terminal portion
30 metal block
40 insulating sheet
50, 501, 502 metal plate portion
50a lower surface (of metal plate portion)
50b side surface (of metal plate portion)
50c upper surface (of metal plate portion)
51 thin portion
52, 521, 522 fastening portion of metal plate portion
53 mounting hole of fastening portion of metal plate portion
57, 573 cooling plate portion
57a, 573a fin
57b seal portion
58 fastening portion of cooling plate portion
59 mounting hole of fastening portion of cooling plate portion
60 resin molded portion
62 extended side portion
66 rib portion
70 grease
80 solder layer
82 solder layer
100 channel forming member
102 cooling media channel
110 bolt
120 sealing member
600 hybrid system
602 battery
610 inverter
612 IPM
616 DC-DC booster transformer
620, 622 motor generator

The invention claimed is:
1. A semiconductor module comprising:
a semiconductor device;
a metal plate portion that includes a first surface on a side of the semiconductor device;
a molded portion that is formed by molding a resin on the semiconductor device and the metal plate portion;
a cooling plate portion that is a separate member from the metal plate portion, is provided on a side opposite to the first surface on the side of the semiconductor device, and includes fins on a side opposite to the side of the metal plate portion;
a heat sink part that is provided between the semiconductor device and the first surface of the metal plate portion on the side of the semiconductor device; and
an insulating material that is provided between the heat sink part and the first surface of the metal plate portion on the side of the semiconductor device;
the heat sink part and the insulating material are disposed in the molded portion
the insulating material includes an end that extends outwardly with respect to an end of the heat sink part, and
the fins of the metal plate portion are formed at a center side with respect to the end of the heat sink part,
wherein the metal plate portion includes fastening portions provided at opposite ends thereof in a first direction,
the fastening portions of the metal plate portion are formed to have a thickness smaller than a center portion of the metal plate portion, and
the fastening portion of one end of the metal plate portion in the first direction is coplanar with the first surface of the metal plate portion on the side of the semiconductor device, and the fastening portion of another end of the metal plate portion in the first direction is coplanar with a second surface of the metal plate portion on the side of the cooling plate portion.

* * * * *